US009115408B2

(12) United States Patent
Fields et al.

(10) Patent No.: US 9,115,408 B2
(45) Date of Patent: Aug. 25, 2015

(54) **RAPID *SALMONELLA* SEROTYPING ASSAY**

(71) Applicant: Centers for Disease Control and Prevention, Atlanta, GA (US)

(72) Inventors: Patricia Fields, Decatur, GA (US); John R. McQuiston, Decatur, GA (US); Collette Fitzgerald Leaumont, Lawrenceville, GA (US)

(73) Assignee: The United States of America as represented by the Secretary, Department of Health and Human Services, Centers for Disease Control and Prevention, Washington, DC (US)

( * ) Notice: Subject to any disclaimer, the term of this patent is extended or adjusted under 35 U.S.C. 154(b) by 36 days.

(21) Appl. No.: 13/871,098

(22) Filed: Apr. 26, 2013

(65) Prior Publication Data

US 2013/0280714 A1 Oct. 24, 2013

Related U.S. Application Data

(63) Continuation-in-part of application No. 13/877,467, filed as application No. PCT/US2011/057875 on Oct. 26, 2011.

(60) Provisional application No. 61/406,797, filed on Oct. 26, 2010.

(51) Int. Cl.
*C12Q 1/68* (2006.01)

(52) U.S. Cl.
CPC ............ *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 5,580,730 A | 12/1996 | Okamoto | |
| 6,649,414 B1 | 11/2003 | Chandler et al. | |
| 6,939,720 B2 | 9/2005 | Chandler et al. | |
| 2003/0157696 A1 | 8/2003 | Agron et al. | |
| 2010/0279278 A1* | 11/2010 | Labgold | 435/6 |

FOREIGN PATENT DOCUMENTS

| | | |
|---|---|---|
| EP | 1739193 A2 | 1/2007 |
| WO | WO-9500664 A1 | 1/1995 |
| WO | WO-2012058303 A2 | 5/2012 |

OTHER PUBLICATIONS

Yoshida et al. (Methodologies towards the development of an oligonucleotide microarray for determination of *Salmonella* serotypes, Journal of Microbiological Methods 70 (2007) 261-271).*

Munoz et al. (Development and Evaluation of a Multiplex Real-Time Polymerase Chain Reaction Procedure to Clinically Type Prevalent *Salmonella enterica* Serovars, Journal of Molecular Diagnostics, vol. 12, No. 2, Mar. 2010).*
Fields (*Salmonella* Serotyping, 10th Annual PulseNet Update Meeting, Apr. 5, 2006).*
Tennant et al. (Identification by PCR of Non-typhoidal *Salmonella enterica* Serovars Associated with Invasive Infections among Febrile Patients in Mali, PLoS Negl Trop Dis 4(3): e621, Mar. 19, 2010).*
Levy et al. (PCR Method to Identify *Salmonella enterica* Serovars Typhi, Paratyphi A, and Paratyphi B among *Salmonella* Isolates from the Blood of Patients with Clinical Enteric Fever, Journal of Clinical Microbiology, May 2008, p. 1861-1866).*
Fitzgerald et al. (Multiplex, Bead-Based Suspension Array for Molecular Determination of Common *Salmonella* Serogroups, Journal of Clinical Microbiology, Oct. 2007, p. 3323-3334).*
Rozen et al. (Primer3 on the WWW for General Users and for Biologist Programmers, in Methods in Molecular Biology, vol. 132: Bioinformatics Methods and Protocols, 2000).*
Wang et al. (The *Escherichia coli* O111 and *Salmonella enterica* O35 Gene Clusters: Gene Clusters Encoding the Same Colitose-Containing O Antigen Are Highly Conserved, Journal of Bacteriology, Sep. 2000, p. 5256-5261).*
NCBI Accession No. AF285969 (Aug. 2, 2001).*
Hong et al. (Rapid screening of *Salmonella enterica* serovars Enteritidis, Hadar, Heidelberg and Typhimurium using a serologically-correlative allelotyping PCR targeting the O and H antigen alleles, BMC Microbiology 2008, 8:178 doi:10.1186/1471-2180-8-178).*
Hong et al. (A Rapid Screen of Broth Enrichments for *Salmonella enterica* Serovars Enteritidis, Hadar, Heidelberg, and Typhimurium by Using an Allelotyping MultiplexPCR That Targets O- and H-Antigen Alleles, Journal of Food Protection, vol. 72, No. 10, 2009, pp. 2198-2201).*
Lim et al. (Application of PCR-based serogrouping of selected *Salmonella* serotypes in Malaysia, J Infect Dev Ctries 2009; 3(6):420-428.).*
Hirose et al. (Selective Amplification of tyv (rfbE), prt (rfbS), viaB, and fliC Genes by Multiplex PCR for Identification of *Salmonella enterica* Serovars Typhi and Paratyphi A, Journal of Clinical Microbiology, Feb. 2002, p. 633-636).*
Perera et al. (Development of a PCR assay for the identification of *Salmonella enterica* serovar Brandenburg, Journal of Medical Microbiology (2008), 57, 1223-1227).*
Fitzgerald et al. (Molecular Analysis of the rfb O Antigen Gene Cluster of *Salmonella enterica* Serogroup O:6,14 and Development of a Serogroup-Specific PCR Assay, Appl. Environ. Microbiol. 2003, 69(10):6099).*
Samuel et al. (Relationships of the *Escherichia coli* O157, O111, and O55 O-Antigen Gene Clusters with Those of *Salmonella enterica* and *Citrobacter freundii*, Which Express Identical O Antigens, J. Bacteriol. 2004, 186(19):6536).*

(Continued)

*Primary Examiner* — Stephanie K Mummert
*Assistant Examiner* — Aaron Priest
(74) *Attorney, Agent, or Firm* — Gifford, Krass, Sprinkle, Anderson & Citkowski, P.C.; Weston R. Gould

(57) ABSTRACT

Processes for the serotype specific detection and identification of one or more *Salmonella* serotypes are provided. A family of specific primers and probes are provided that allow screening of biological or environmental samples for robust, rapid, and reproducible detection and identification of one or more *Salmonella* serotypes in the sample.

7 Claims, 10 Drawing Sheets

(56) References Cited

OTHER PUBLICATIONS

Li et al. (Structural and genetic relationships of two pairs of closely related O-antigens of*Escherichia coli* and*Salmonella enterica*: *E. coli* O11/*S. enterica* O16 and*E. coli* O21/*S. enterica* O38, FEMS Immunol Med Microbiol 61 (Jan. 18, 2011) 258-268).*

Fitzgerald C., et al., "Multiplex, Bead-based Suspension Array for Molecular Determination of Common *Salmonella* Serogroups," Journal of Clinical Microbiology, 45(10):3323-3334, Jul. 2007.

Tennant S., et al., "Identification by PCR of Non-typhoidal *Salmonella* Enteric Serovars Associated with Invasive Infections Among Febrile Patients in Mali," PLoS Neglected Tropical Diseases, 4(3):e621, Mar. 2010.

Malorny B., et al., "A Real-time PCR for the Detection of *Salmonella* Enteritidis in Poultry Meat and Consumption Eggs," Journal of Microbiological Methods, 70:245-251, Apr. 2007.

Malorny B., et al., "Molecular Characterization of *Salmonella* Strains by an Oligonucleotide Multiprobe Microarray," Molecular and Cellular Probes, 21:56-65, Sep. 2006.

Feder I., et al., "Comparison of Cultivation and PCR-hybridization for Detection of *Salmonella* in Porcine Fecal and Water Samples," Journal of Clinical Microbiology, 39(7):2477-2484, Jul. 2001.

International Search Report for PCT/US2011/057875 dated Aug. 1, 2012.

Baker S., et al., "A Novel Linear Plasmid Mediates Flagellar Variation in *Salmonella* Typhi," PLoS Pathog 3:e59, 2007.

Boyd E.F., et al., "Molecular Genetic Relationships of the *Salmonellae*," Appl Environ Microbiol, 62:804-808, 1996.

Echeita M., et al., "Multiplex PCR-based Detection and Identification of the Most Common *Salmonella* Second-phase Flagellar Antigens," Res Microbiol, 153:107-113, 2002.

Ewing W.H., "The Nomenclature of *Salmonella*, Its Usage, and Definitions for the Three Species," Can J Microbiol, 18:1629-1637, 1972.

Frankel G., "Intragenic Recombination in a Flagellin Gene: Characterization of the H1-j Gene of *Salmonella typhi*," EMBO Journal, 8:3149-3152, 1989.

Garaizar J., et al., "DNA Microarray-based Typing of an Atypical Monophasic *Salmonella enterica* Serovar," J Clin Microbiol, 40:2074-2078, 2002.

Grimont P.A.D., et al., "Antigenic Formulae of the *Salmonella* Serovars," WHO Collaborating Centre for Reference and Research on *Salmonella*, 2007.

Guibourdenche M., et al., "Supplement 2003-2007 (No. 47) to the White-Kauffmann-Le Minor scheme," Res Microbiol, 2009.

He X., et al., "Hypervariable Region IV of *Salmonella* gene fliC$^d$ Encodes a Dominant Surface Epitope and a Stabilizing Factor for Functional Flagella," J Bacteriol, 176(8):2406-2414, 1994.

Herrera-Leon S., et al., "Multiplex PCR for Distinguishing the Most Common Phase-1 Flagellar Antigens of *Salmonella* spp.," J Clin Microbiol, 42(6):2581-2586, 2004.

Hirose K., et al., "Selective Amplification of tyv (rfbE), prt (rfbS), viaB, and fliC Genes by Multiplex PCR for Identification of *Salmonella enterica* Serovars *Typhi* and *Paratyphi A*," J Clin Microbiol, 40:633-636, 2002.

Joys T.M., "The Covalent Structure of the Phase-1 Flagellar Filament Protein of *Salmonella typhimurium* and Its Comparison with other Flagellins," Journal of Biological Chemistry, 260:15758-15761, 1985.

Joys T.M., "Recombination in H1, the Gene Determining the Flagellar Antigen-i of *Salmonella Typhimurium*; Mapping of H1 and fla Mutations," Journal of General Biological, 58:267-275, 1969.

Kauffmann F., "The Bacteriology of Enterobacteriaceae," 1 ed, vol. The Williams and Wilkins Company, Baltimore, 1966.

Leader B.T., et al., "High-throughput Molecular Determination of *Salmonella enterica* Serovars by Use of Multiplex PCR and Capillary Electrophoresis Analysis," J Clin Microbiol, 47(5):1290-1299, 2009.

MacNab R.M., "Flagella and Motility," p. 123-145. In F.C. Neidhardt (ed.), *Escherichia coli* and *Salmonella* Cellular and Molecular Biology, 2 ed. vol. 1. ASM Press, Washington, DC, 1996.

MacNab R.M., "Genetics and Biogenesis of Bacterial Flagella," Annu Rev Genet, 26:131-158, 1992.

Masten B.J., et al., Molecular Analyses of the *Salmonella* g . . . Flagellar Antigen Complex [published erratum appears in J Bacteriol May 1994, 176(9):2771]; Journal of Bacteriology, 175:5359-5365, 1993.

McQuiston J.R., et al., "Do *Salmonella* Carry Spare Tyres?" Trends Microbiol, 16:142-148, 2008.

McQuiston J.R., "Molecular Phylogeny of the *Salmonellae*: Relationships Among *Salmonella* Species and Subspecies Determined from Four Housekeeping Genes and Evidence of Lateral Gene Transfer Events," J Bacteriol, 190(21):7060-7067, 2008.

McQuiston J.R., et al., "Sequencing and Comparative Analysis of Flagellin Genes fliC, fljB, and flpA from *Salmonella*," J Clin Microbiol, 42:1923-1932, 2004.

Microbiology S., S.o.t.l.S.o, "The Genus *Salmonella* Lignières, 1900," Journal of Hygiene, 22:333-350, 1934.

Popoff M.Y., et al., "Supplement 2002 (No. 46) to the Kauffmann-White Scheme," Res Microbiol, 155:568-570, 2004.

Prevention, C.f.D.C.a 2004, posting date. "*Salmonella*: Annual Summary," Department of Health and Human Services, 2004 [online].

Prokaryotes, J.C.o.t.l.C.o.S.o. 2005. "The Type Species of the Genus *Salmonella* Lignières 1900 is *Salmonella enterica* (ex Kauffman and Edwards 1952) Le Minor and Popoff 1987, with the Type Strain LT2T, and Conservation of the Epithet *enterica* in *Salmonella enterica* Over All Earlier Epithets that May Be Applied to this Species," Opinion 80, Int. J Syst Evol Microbiol, 55:519-520, 2005.

Reeves M.W., et al., "Clonal Nature of *Salmonella* Typhi and Its Genetic Relatedness to Other *Salmonellae* as Shown by Multilocus Enzyme Electrophoresis, and Proposal of *Salmonella bongori* comb. nov.," J Clin Microbiol, 27:313-320, 1989.

Services, D.o.H.a.H. "*Salmonella*: Annual Summary 2001," Centers for Disease Control and Prevention, 2001.

Silverman M., et al., "Phase Variation: Genetic Analysis of 45 Switching Mutants," Cell, 19:845-854, 1980.

Silverman M., et al., "Phase Variation in *Salmonella*: Genetic Analysis of a Recombinational Switch," Proc Natl Acad Sci USA, 76:391-395, 1979.

Smith N. H., et al., "Molecular Genetic Basis for Complex Flagellar Antigen Expression in a Triphasic Serovar of *Salmonella*," Proc Natl Acad Sci USA, 88:956-960, 1991.

Tindall B.J., et al., "Nomenclature and Taxonomy of the Genus *Salmonella*," Int J Syst Evol Microbiol, 55:521-524, 2005.

Trafny E.A., et al., "A Novel Multiplex PCR Assay for the Detection of *Salmonella enterica* Serovar Enteritidis in Human Feces," Lett Appl Microbiol, 43:673-679, 2006.

Vanegas R.A., et al., "Molecular Analyses of the Phase-2 Antigen Complex 1,2, . . . of *Salmonella* spp.," J Bacteriol, 177(13):3863-3864, 1995.

Wei L.N., et al., "Covalent Structure of Three Phase-1 Flagellar Filament Proteins of *Salmonella*," J Mol Biol, 186:791-803, 1985.

Wei L.N., et al., "The Nucleotide Sequence of the H-1r Gene of *Salmonella* Rubislaw," Nucleic Acids Res, 14:8227, 1986.

McQuiston J.R., et al., "Molecular Determination of H Antigens of *Salmonella* by Use of a Microsphere-based Liquid Array," J Clin Microbiol, 49(2):565-573, 2011.

Karlin S., et al., "Methods for Assessing the Statistical Significance of Molecular Sequence Features by Using General Scoring Schemes," PNAS, 87:2264-2268, 1990.

Karlin S., et al., "Applications and Statistics for Multiple High-Scoring Segments in Molecular Sequences," PNAS, 90:5873-5877, 1993.

Altschul S.F., et al., "Basic Local Alignment Search Tool," J Nol Biol, 215(3):403-410, 1990.

Altschul S.F., et al., "Gapped BLAST and PSI-BLAST: A New Generation of Protein Database Search Programs," Nucleic Acids Research, 25(17):3389-3402, 1997.

Meyers E., et al., "Optimal Alignments in Linear Space," CABIOS, 4(1):11-17, 1988.

(56) References Cited

OTHER PUBLICATIONS

Saiki R., et al., "A Novel Method for the Detection of Polymorphic Restriction Sites by Cleavage of Oligonucleotide Probes: Application to Sickle-Cell Anemia," Nature Biotechnology, 3:1008-1012, 1985.

Conner B., et al., "Detection of Sickle Cell beta S-globin Allele by Hybridization with Synthetic Oligonucleotides," PNAS, 80:278-282, 1983.

Landegren U., et al., "A Ligase-Mediated Gene Detection Technique," Science, 241:1077, 1988.

Ortiz A., et al., "A Rapid Method for Detecting Specific Amplified PCR Fragments in Microtiter Plates," Nucleic Acids Res., 24(16):3280-3281, 1996.

Lishanski A., et al., "Branch Migration Inhibition in PCR-Amplified DNA: Homogeneous Mutation Detection," Nucleic Acids Res., 29(9):e42, 2000.

Lee K., et al., "A Colorimetric Confirmation Method for DNA Amplification in PCR and Its Application to the Detection of *Giardia lamblia* Cysts," Biotechnology Letters, 25(20):1739-1742, 2003.

Kunkel T., "DNA Replication Fidelity," Journal of Biological Chemistry, 267(26):18251-18254, 1992.

McQuiston J.R., et al., "Sequencing and Comparative Analysis of Flagellin Genes fliC, fljB, and flpA from *Salmonella*," Journal of Clinical Microbiology, 42(5):1923-1932, 2004.

Li Q. et al., "Genetic Variation of dTDP-L-rhamnose Pathway Genes in *Salmonella enterica*," Microbiology, 146:2291-2307, 2000.

Landegren U., et al., "DNA Diagnostics—Molecular Techniques and Automation," Science, 242(4876):229-237, 1988.

Johnson K.A., et al., "Conformational Coupling in DNA Polymerase Fidelity," Journal of Biological Chemistry, 62:685-713, 1993.

International Search Report and Written Opinion for co-pending application No. PCT/US2013/038830 dated Dec. 11, 2013.

\* cited by examiner

O Group raw data

A

| Description | Para A | GRP D | GRP B | GRP C1 | GRP C2 | GRP E | GRP G | O:6,14 | O:11 | O:16 | O:35 | O:50 |
|---|---|---|---|---|---|---|---|---|---|---|---|---|
| Neg Cont. 09 H | 139 | 134 | 144 | 172 | 186 | 157.5 | 205 | 166 | 116 | 173 | 127 | 130 |
| 08_0008 A a:[1,5] | 10795 | 136.5 | 168 | 141.5 | 184 | 162.5 | 153 | 148 | 164 | 115 | 136 | 120 |
| 08_0018 D d:- | 126 | 3813 | 129 | 159 | 142 | 132.5 | 167 | 158 | 86 | 58 | 124 | 361 |
| 08_0284 B f,g,s:- | 143 | 146 | 10725 | 97 | 146 | 211 | 151 | 129 | 95 | 187 | 124 | 220 |
| 08_0109 C1 y:1,5 | 154 | 148.5 | 135 | 4595 | 181 | 183 | 156 | 112 | 47 | 194 | 99 | 225 |

B

| Description | Para A | GRP D | GRP B | GRP C1 | GRP C2 | GRP E | GRP G | O:6,14 | O:11 | O:16 | O:35 | O:50 |
|---|---|---|---|---|---|---|---|---|---|---|---|---|
| Neg Cont. 09 H | 1 | 1 | 1 | 1 | 1 | 1 | 1 | 1 | 1 | 1 | 1 | 1 |
| 08_0008 A a:[1,5] | 78 | 1 | 1 | 1 | 1 | 1 | 1 | 1 | 1 | 1 | 1 | 1 |
| 08_0018 D d:- | 1 | 28 | 1 | 1 | 1 | 1 | 1 | 1 | 1 | 0 | 1 | 3 |
| 08_0284 B f,g,s:- | 1 | 1 | 74 | 1 | 1 | 1 | 1 | 1 | 1 | 1 | 1 | 2 |
| 08_0109 C1 y:1,5 | 1 | 1 | 1 | 27 | 1 | 1 | 1 | 1 | 0 | 1 | 1 | 2 |

| Description | a | b | c | d | y | 1 | 2 | 5 | 6 | 7 | G | m | z4 | f | s |
|---|---|---|---|---|---|---|---|---|---|---|---|---|---|---|---|
| Neg Cont 09 H | 66 | 26 | 38 | 46 | 77 | 30 | 56 | 112 | 36 | 38 | 42 | 62 | 92 | 378 | 39 |
| 08_0008 A a [1,5] | 5324 | 60 | 65 | 81 | 42 | 817 | 80 | 1021 | 76 | 21 | 48 | 121 | 84 | 375 | 68 |
| 08_0018 D d - | 124 | 34 | 95 | 6667 | 122 | 61 | 145 | 74 | 90 | 86 | 67 | 103 | 151 | 353 | 80 |
| 08_0264 B f,g,s,- | 143 | 112 | 118 | 63 | 82 | 66 | 69 | 109 | 42 | 71 | 3298 | 137 | 153 | 6769 | 2015 |
| 08_0109 C1 y 1,5 | 41 | 48 | 89 | 112 | 7071 | 7323 | 80 | 6028 | 52 | 68 | 63 | 83 | 132 | 447 | 59 |

B

| Description | a | b | c | d | y | 1 | 2 | 5 | 6 | 7 | G | m | z4 | f | s |
|---|---|---|---|---|---|---|---|---|---|---|---|---|---|---|---|
| Neg Cont 09 H | 1 | 1 | 1 | 1 | 1 | 1 | 1 | 1 | 1 | 1 | 1 | 1 | 1 | 1 | 1 |
| 08_0008 A a [1,5] | 81 | 2 | 2 | 1 | 1 | 28 | 1 | 9 | 2 | 1 | 1 | 2 | 1 | 1 | 2 |
| 08_0018 D d - | 2 | 1 | 2 | 145 | 2 | 2 | 3 | 1 | 3 | 2 | 2 | 2 | 2 | 1 | 2 |
| 08_0264 B f,g,s,- | 2 | 1 | 3 | 2 | 1 | 2 | 1 | 1 | 1 | 2 | 79 | 2 | 2 | 18 | 52 |
| 08_0109 C1 y 1,5 | 1 | 2 | 2 | 2 | 92 | 248 | 1 | 54 | 1 | 2 | 2 | 1 | 2 | 1 | 2 |

FIG. 6

| Rank | Serotype | O | H1 | H2 | Rank | Serotype | O | H1 | H2 |
|---|---|---|---|---|---|---|---|---|---|
| 1 | Typhimurium | | | | 51 | Ohio | | | |
| 2 | Enteritidis | | | | 52 | Bleckley | | | |
| 3 | Newport | | | | 53 | Kiambu | | | |
| 4 | Heidelberg | | | | 54 | Uganda | | | |
| 5 | Javiana | | | | 55 | Urbana | | | |
| 6 | Montevideo | | | | 56 | 14[5],12:b:- | | | |
| 7 | Muenchen | | | | 57 | Minnesota | | | |
| 8 | 14,[5],12:i:- | | | | 58 | Inverness | | | |
| 9 | Saintpaul | | | | 59 | Hvittingfoss | | | |
| 10 | Oranienburg | | | | 60 | Bardo | | | |
| 11 | Braenderup | | | | 61 | Bredeney | | | |
| 12 | Infantis | | | | 62 | London | | | |
| 13 | Mississippi | | | | 63 | Telelkebir | | | |
| 14 | Thompson | | | | 64 | Havana | | | |
| 15 | Agona | | | | 65 | Johannesburg | | | |
| 16 | Paratyphi B var. L(+) tartrate+ | | | | 66 | Cerro | | | |
| 17 | Typhi | | | | 67 | Albany | | | |
| 18 | Berta | | | | 68 | Chester | | | |
| 19 | Hadar | | | | 69 | Worthington | | | |
| 20 | Stanley | | | | 70 | Indiana | | | |
| 21 | Poona | | | | 71 | Istanbul | | | |
| 22 | Bareilly | | | | 72 | Oslo | | | |
| 23 | Anatum | | | | 73 | Agbeni | | | |
| 24 | Hartford | | | | 74 | Grumpensis | | | |
| 25 | Mbandaka | | | | 75 | IV 48:g,z51:- | | | |
| 26 | Parama | | | | 76 | Alachua | | | |
| 27 | Paratyphi B | | | | 77 | Cubana | | | |
| 28 | Litchfield | | | | 78 | Haardt | | | |
| 29 | Sandiego | | | | 79 | Eastbourne | | | |
| 30 | Schwarzengrund | | | | 80 | Lomalinda | | | |
| 31 | Derby | | | | 81 | IV 50:z4,z23:- | | | |
| 32 | Paratyphi A | | | | 82 | Edinburg | | | |
| 33 | Tennessee | | | | 83 | Othmarschen | | | |
| 34 | Brandenburg | | | | 84 | Baildon | | | |
| 35 | Senftenberg | | | | 85 | Ealing | | | |
| 36 | Norwich | | | | 86 | IV 50:g,z51:- | | | |
| 37 | Rubislaw | | | | 87 | Monschaui | | | |
| 38 | Give | | | | 88 | IV 44:z4,z23:- | | | |
| 39 | Miami | | | | 89 | Choleraesuis | | | |
| 40 | Gaminara | | | | 90 | Meleagridis | | | |
| 41 | Weltevreden | | | | 91 | Kottbus | | | |
| 42 | Bovismorbificans | | | | 92 | Kintambo | | | |
| 43 | Kentucky | | | | 93 | Corvallis | | | |
| 44 | Virchow | | | | 94 | 19,12:l,z28:- | | | |
| 45 | Muenster | | | | 95 | Ibadan | | | |
| 46 | Dublin | | | | 96 | Rissen | | | |
| 47 | Manhattan | | | | 97 | IIIa 18:z4,z23:- | | | |
| 48 | Pomona | | | | 98 | Nima | | | |
| 49 | Reading | | | | 99 | Irumu | | | |
| 50 | Adelaide | | | | 100 | Pensacola | | | |

FIG. 8

RAPID *SALMONELLA* SEROTYPING ASSAY

CROSS REFERENCE TO RELATED APPLICATIONS

This application is a continuation-in-part of U.S. patent application Ser. No. 13/877,467, filed Apr. 3, 2013, which is a U.S. National Phase of PCT/US2011/057875 filed Oct. 26, 2011, and which depends from and claims priority to U.S. Provisional Application No. 61/406,797, filed Oct. 26, 2010, the entire contents of each of which are incorporated herein by reference.

GOVERNMENT INTEREST

The invention described herein may be manufactured, used, and licensed by or for the United States Government.

FIELD OF THE INVENTION

Processes and compositions are provided for detection of organisms in fluid samples. More specifically, the invention relates to selective detection and serotyping of *Salmonella* in biological or other fluid media. Processes are described for rapid and sensitive detection of *Salmonella*, including *Salmonella* ser. Enteritidis in human, animal, food, and environmental samples and quantification thereof. Diagnostic kits are provided for identification of *Salmonella* serotypes in a clinical, laboratory, or field setting.

BACKGROUND OF THE INVENTION

Detecting and serotyping *Salmonella* is essential to protecting the food supply and for understanding the epidemiology of this important food-borne pathogen. Determining the presence and serotype of the dangerous *Salmonella* ser. Enteritidis is of particular importance to the poultry and egg industries.

The genus *Salmonella* is divided into two species, *S. enterica* and *S. bongori* (33). *S. enterica* is further divided into seven subspecies that can be abbreviated by Roman numerals, I, II, IIIa, IIIb, IV, VI and VII. Subsp. VII was described by Multilocus Enzyme Electrophoresis (MLEE) and by phylogenetic analysis of housekeeping genes (2, 9 22). Subspecies V is now recognized as the separate species, *S. bongori* (28).

Serotyping further divides the *Salmonellae* subspecies into subtypes, or serovars (ser.), by immunologic characterization of two surface structures, O-polysaccharide (O-antigen) and flagellin protein (H-antigen) (25, 27). The current standard for *Salmonella* serotyping is the Kauffmann-White serotyping scheme. This method currently includes the recognized 2,587 serotypes (4, 8, 9). A serotype is represented by an antigenic formula (e.g. I 4,5,12:i:1,2) indicating the subspecies; and O, Phase 1 H, and Phase 2 H antigens. Serotypes in subspecies I are also given a name (e.g. Typhimurium).

Over 30,000 culture confirmed cases of *Salmonella* are identified in the United States each year. The production and quality control of the greater than 250 antisera required to generate the >2,500 serotypes using current methods is difficult and time consuming. Many isolates require three to five days or more to fully determine the serotype, which delays serotype submission to the public health data information systems. Improving the rate and accuracy of detecting and serotyping *Salmonella* in samples is essential to improving product safety. Thus, there is a need for compositions and methods useful to improve detection of and serotyping of *Salmonella*, especially within food.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Processes are provided for detecting the presence or absence of *Salmonella* in a sample and for serotyping *Salmonella* in a sample. Detection and serotyping can be performed simultaneously. Processes include performing an O-grp-2 assay by adding to a sample one or more O-grp-2 primer sets operable to produce an O-grp-2 amplification product of an O-grp-2 target sequence, where the primer set comprises a forward primer and a reverse primer that hybridize to regions flanking a target sequence under conditions suitable for a polymerase chain reaction, and detecting the presence of or absence of the amplification product by hybridization of a probe specific to the amplification product. A probe comprises a nucleotide sequence selected from the group of SEQ ID NOs: 131, 132, 133, 134, and 135.

The assay is optionally performed in a multiplex format whereby primers for O-grp-1 and optionally H-ag, and/or O-grp-1 are combined in the same sample simultaneously. The process optionally further include determining the identity of the O-grp-1 amplification product by identification of the probe specific to the detected O-grp-1 amplification product, the identity of the H-ag amplification product by identification of the probe specific to the detected H-ag amplification product. Optionally, the process further includes determining the identity of the O-grp-2 amplification product by identification of the probe specific to the detected O-grp-2 amplification product.

Primers and probes are provided with sequences operable to amplify one or more target sequences or to specifically hybridize with one or more amplification products for identification of the presence or absence or serotyping *Salmonella* in the sample. The primers and probes are optionally combined in a kit or a library.

BRIEF DESCRIPTION OF THE DRAWINGS

FIG. 5 illustrates raw MFI data illustrating specific detection of O-grp-1 serotype in a sample (A) and the ratio of positives to negative control for the detected isolates (B);

FIG. 6 illustrates raw MFI data illustrating specific detection of H-ag serotype included in a sample (A); and the ratio of positives to negative control for the isolates (B);

FIG. 8 illustrates overall detection of the 100 most common serotypes; and

DETAILED DESCRIPTION OF EMBODIMENTS OF THE INVENTION

Figure 1:
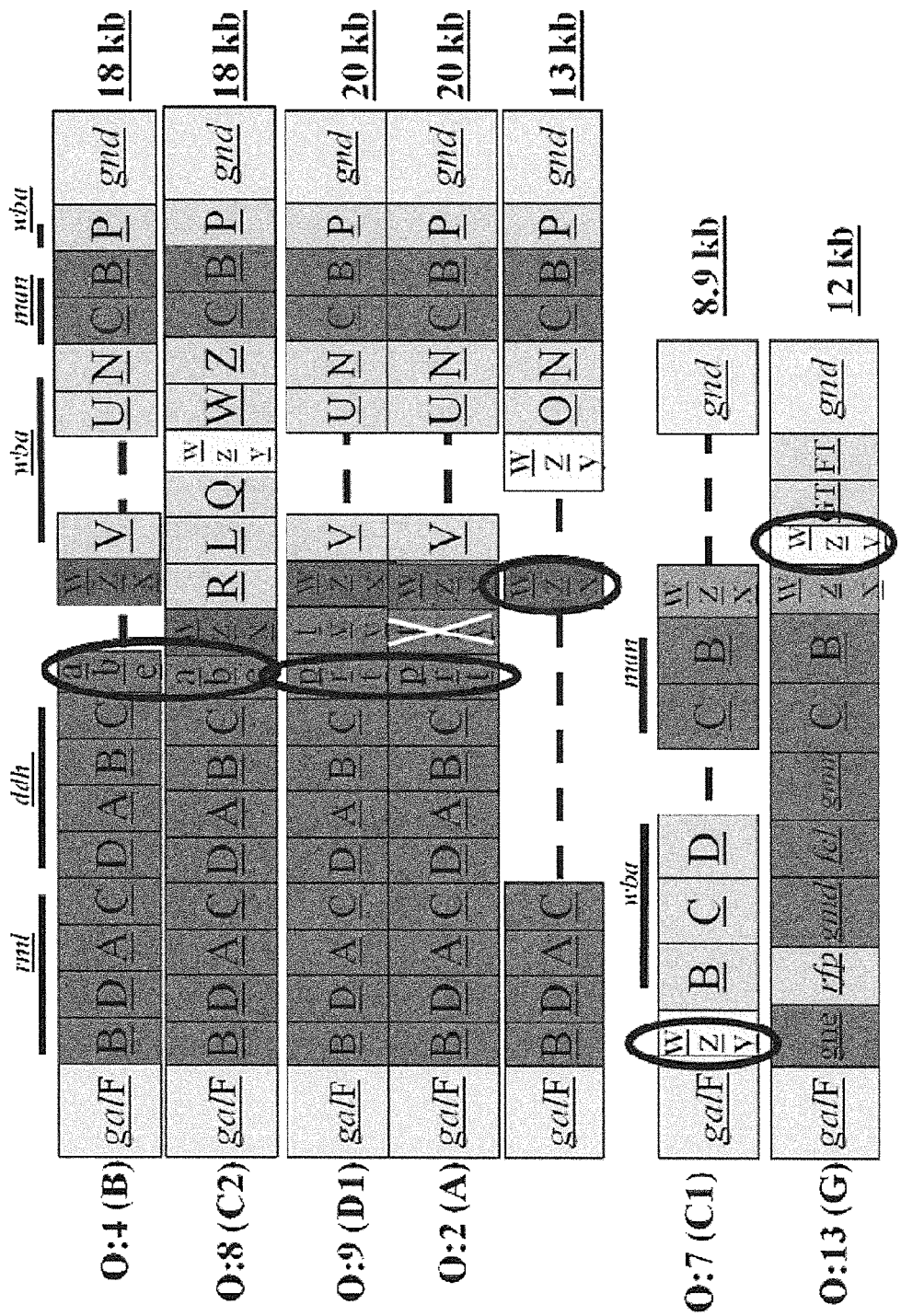
FIG. 1 illustrates rfb gene clusters targeted in some embodiments of an O-grp-1 assay.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The invention has utility for the detection and serotyping of *Salmonella* in a sample. As it is difficult, expensive, and time consuming to regularly perform the traditional serotyping culture assays, the sensitive PCR based techniques herein provide a more reliable detection method than other currently employed assay systems.

Processes and reagents are described that allow rapid screening of a sample for the presence of one or more *Salmonella* organisms as well as specific serotyping thereof by rapidly and reliably determining the type of O and H antigens.

The H antigens of *Salmonella* are primarily encoded by one of two genes, fliC or fljB, which express the Phase 1 H antigen and the Phase 2 H antigen, respectively. The fliC gene is located in one of the flagellar biosynthesis operons. fliC is present in all Salmonellae and has a homologue in other enteric bacteria. The fljB gene is located in a region of the genome that is unique to *Salmonella enterica* and is present in four of the *S. enterica* subspecies (Subsp. I, II, IIIb, and VI). The two flagellin loci, fliC and fljB, are coordinately regulated so that only one antigen is expressed at a time in a single cell via a phase variation mechanism (31). Serotypes expressing two flagellin types are termed diphasic, while those with only one flagellar antigen type are considered monophasic. Subspecies IIIa, IV, VII and *S. bongori* do not contain the fljB operon and are monophasic. In rare instances, *Salmonella* isolates express a third flagellar antigen and the serotype is referred to as triphasic (1, 32).

There are currently 114 recognized H antigen types described in the Kauffmann-White scheme (23). Sixty-nine flagellar antigens are characterized by a single epitope that typically shows little or no immunologic relatedness with other H antigens (e.g., H:a; b; c; d). The remaining H antigens have been described having multiple epitopes and are grouped into antigenically related complexes. Antigen complexes account for 45 H antigens in the serotyping scheme and consist of a major common epitope plus one or more secondary epitopes. The antigen complexes are named based on the major immunologic epitope (e.g. 1-complex, EN-complex, G-complex, L-complex and Z4-complex). For example, the 1 complex is identified by the major antigen H:1 and further subdivided by the secondary epitopes, H:2; 5; 6 or 7. Therefore, an antigen could be represented as H:1,2; 1,5 1,6 or 1,7 as well as combinations of these single factors such as H:1,5,7 (16). Eight antigens are recognized in the 1-complex (e.g. H:1,2; 1,5 . . . ), four in the Z4-complex (e.g. H:z4,z23; z4,z24 . . . ), three in the EN-complex (e.g. H:e,n,x; e,n,z15; e,n,x,z15), six in the L-complex (e.g. H:1,v; 1,w; 1,z13 . . . ) and 21 antigens in the G-complex (f,g,t; g,m . . . ).

The O antigen contains multiple repeats of an oligosaccharide unit (O unit), which, together with lipid A and core oligosaccharides, form the lipopolysaccharide present in the outer membranes of gram-negative bacteria. Many of the genes required for O-antigen biosynthesis are organized in a large regulon termed the rfb gene cluster. Typically, three classes of genes are found in rfb clusters: (i) genes for synthesis of nucleotide sugars specific to the respective O antigen; (ii) sugar transferase genes to build the O subunit; and (iii) the O-antigen polymerase (wzy) and transport protein (wzx) genes for assembly of the O subunit into the O antigen.

There are 46 O serogroups described in the Kauffmann-White scheme. Under this scheme serogroups were originally designated by alphabetic letters. Later it was necessary to continue with numbers 51 to 67. The antigenic differences among the 46 *Salmonella* O serogroups are due mainly to genetic variation in their respective rfb gene clusters.

Compositions and methods are provided for the sensitive detection of *Salmonella* in samples, such as biological or environmental samples, using techniques involving PCR. Primers are provided that amplify regions of the rfb region for O-antigens and fliB and fliC for H antigens with high specificity and broad serotype recognition that are subsequently detectable in sensitive detection systems.

The following definitional tell is are used throughout the specification without regard to placement relative to these terms.

As used herein, the term "variant" defines either a naturally occurring genetic mutant of *Salmonella*, or a *Salmonella* gene or a recombinantly prepared variation of *Salmonella*, or a *Salmonella* gene, with one or more mutations or modifications in a gene compared to the sequence wild-type sequence. The term "variant" may also refer to either a naturally occurring variation of a given nucleic acid sequence or a recombinantly prepared variation of a given nucleic acid sequence in which one or more nucleic acids have been replaced by substitution, addition, or deletion.

As used herein, the term "analog" in the context of a non-proteinaceous analog defines a second organic or inorganic molecule that possesses a similar or identical function as a first organic or inorganic molecule and is structurally similar to the first organic or inorganic molecule.

As used herein, the term "derivative" in the context of a non-proteinaceous derivative defines a second organic or inorganic molecule that is formed based upon the structure of a first organic or inorganic molecule. A derivative of a molecule includes, but is not limited to, a molecule modified, e.g., by the addition or deletion of a hydroxyl, methyl, ethyl, carboxyl or amine group. An organic molecule may also be illustratively esterified, alkylated, labeled, and/or phosphorylated. A derivative also defined as a molecule including a degenerate base illustratively that mimicking a C/T mix such as that from Glen Research Corporation, Sterling, Va., illustratively LNA-dA or LNA-dT, or other nucleotide modification known in the art or otherwise.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, 95%, or more base pair matches to each other typically remain hybridized to each other.

An "isolated" or "purified" nucleotide or oligonucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide/oligonucleotide having less than about 30%, 20%, 10%, 5%, 2.5%, or 1%, (by dry weight) of contaminating material. When nucleotide/oligonucleotide is produced by chemical synthesis, it is optionally substantially free of chemical precursors or other chemicals, i.e., it is separated from chemical precursors or other chemicals which are involved in the synthesis of the molecule. Accordingly, such preparations of the nucleotide/oligonucleotide have less than about 30%, 20%, 10%, or 5% (by dry weight) of chemical precursors or compounds other than the nucleotide/oligonucleotide of interest. In some embodiments of the present invention, a nucleotide/oligonucleotide is isolated or purified.

As used herein, the term "sample" is a portion of a larger source. A sample is optionally a solid, gaseous, or fluidic. A sample is illustratively an environmental or biological sample. An environmental sample is illustratively, but not limited to water, sewage, soil, or air. A "biological sample" is as sample obtained from a biological organism, a tissue, cell, cell culture medium, or any medium suitable for mimicking biological conditions. Non-limiting examples include, saliva, gingival secretions, cerebrospinal fluid, gastrointestinal fluid, mucous, urogenital secretions, synovial fluid, blood, serum, plasma, urine, feces, cystic fluid, lymph fluid, ascites, pleural effusion, interstitial fluid, intracellular fluid, ocular fluids, seminal fluid, mammary secretions, and vitreal fluid, and nasal secretions, throat or nasal materials, eggs, or other food. Methods of obtaining a sample are known in the art. Illustratively, a sample is whole blood, plasma, or serum that is obtained by venipuncture and optionally processed to obtain the final sample.

As used herein, the term "medium" refers to any liquid or fluid that may or may not contain one or more bacteria. A medium is illustratively a solid sample that has been suspended, solubilized, or otherwise combined with fluid to form a fluidic sample. Non-limiting examples include buffered saline solution, cell culture medium, acetonitrile, trifluoroacetic acid, combinations thereof, or any other fluid recognized in the art as suitable for combination with bacteria or other cells, or for dilution of a biological sample or amplification product for analysis.

To determine the percent identity of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions .times.100%). In some embodiments, the two sequences are the same length.

The determination of percent identity between two sequences can also be accomplished using a mathematical algorithm. A non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

As used herein, the terms "subject" and "patient" are synonymous and refer to a human or non-human animal, optionally a mammal including a human, non-primate such as cows, pigs, horses, goats, sheep, cats, dogs, avian species, and rodents; and a non-human primate such as monkeys, chimpanzees, and apes; and a human, also denoted specifically as a "human subject".

Processes are described that provides a rapid, specific, and sensitive assay for detection of *Salmonella* in samples by amplifying one or more nucleotide sequences by processes similar to the polymerase chain reaction (PCR).

The processes are optionally performed in a multiplex environment for the rapid detection of multiple gene sequences. One or more nucleotide probe sequences are optionally attached to a substrate such as a solid support. A solid support can be used in a variety of physical formats, for example, in solution or suspension, as well as linked or immobilized to other solid supports. A solid support can be composed of a natural or synthetic material, an organic or inorganic material, such as a polymer, resin, metal or glass, and combinations thereof. A suitable solid support can have a variety of physical formats, which can include for example: a membrane; column; a hollow, solid, semi-solid, pore or cavity-containing particle such as a bead; a gel; a fiber, including a fiber optic material; a matrix and sample receptacle. Non-limiting examples of sample receptacles include sample wells, tubes, capillaries, vials and any other vessel, groove or indentation capable of holding a sample. A sample receptacle can be contained on a multi-sample platform, such as a microplate, slide, microfluidics device, and the like. Many suitable supports are known in the art and illustratively include Luminex®-type encoded particles, encoded fiber optic particles, magnetic particles, and glass particles. Covalent interaction of a probe with a solid support is useful for retaining the probe during washing procedures performed in some assay fatmats, thus, producing a robust and accurate signal of the presence of absence of a particular gene sequence.

The methods described herein are optionally performed in a multiplexed format such that a plurality of samples is assayed simultaneously. An illustrative multiplexed format involves using physically and/or chemically coded particles.

Use of coded particles in multiplexed formats has been described, for example, in U.S. Pat. No. 6,649,414 and U.S. Pat. No. 6,939,720. Because the codes allow particles to be distinguished from each other, a plurality of distinct particles can be present in a single reaction mixture, allowing a plurality of different samples or different probes to be assayed simultaneously. Codes on particles can correspond, for example, to sample origins, particular target genes to be assayed, and the like, depending on the experimental goal of the user. The specification provides exemplary methods using Luminex®-type encoded particles as substrates for probes and for subsequent detection methods for example only and not as a limitation on the invention. It is appreciated that one of skill in the art readily envisions other assay formats, either multiplex or uniplex, that are equally applicable for use with the inventive methods and compositions. Other illustrative assay methods include real-time PCR such as that run on the Taqman® system, PCR amplification and sequencing, and specific PCR amplification and detection of amplification products by mass spectrometry.

Inventive methods include a single or tiered method of serotyping an organism in a sample. In some embodiments, a first reaction is performed whereby the O antigen group is detected in combination with detection of particular set of H antigens (H-ag). The O antigen group assays are termed O-grp-1 and O-grp-2. The O-grp-1 includes O groups B, C1, C2, D, E, O13, and serotype Paratyphi A. The O-grp-2 optionally includes groups: O:6,14; O:11; O:16; O:35; O:50; O:17, O18; O21, O28; O30, O38; O40, O44; O47, O48; and O61. It is appreciated that O-grp-1 and O-grp-2 optionally include other serogroups in place of or in addition to those listed herein. A first stage tiered assay examining O-grp-1 and the H antigens group examining fliC and fljB will identify the presence of 95% of all human isolates. Thus, a first stage is examination of O-grp-1 along with H-ag antigens in a multiplex assay. Some samples may not yield a positive result from the first stage assay due to the remaining 5% of possible unscreened serotypes. In such a situation, a second stage assay is optionally performed. In some embodiments, a second stage assay is performed simultaneously with or subsequently to a first stage assay. A second stage optionally screens for the O-grp-2 antigen type. It is appreciated that the term second stage assay is for descriptive purposes alone, and any second stage assay can be performed prior to, simultaneously with, or subsequent to a first stage assay. In addition, any assay described herein can be run as a first stage assay alone or in combination with other assays. It is appreciated that one or more second stage assays may be performed whether a positive result or a negative result are obtained in a first stage assay or second stage assay. It is further appreciated that any second stage assay can be used alone and independent of a first stage assay.

In place of or in addition to a first stage assay or a second stage assay, some embodiments analyze a sample for a specific serotype, illustratively: *Salmonella* ser. Enteritidis; the presence or absence of additional targets (including examination of the targets sdf, Vi, and fljB); a species and subspecies assay; or other specific serotype assay; species or subspecies assay; or combinations thereof.

In some embodiments, during a first stage assay, an oligonucleotide forward primer with a nucleotide sequence complementary to a unique sequence to an O-grp-1 target nucleotide sequence is hybridized to its complementary sequence and extended by methods of the polymerase chain reaction (PCR). Similarly, a reverse oligonucleotide primer complementary to a second strand of and O-grp-1 target DNA in the same or an alternate gene region is hybridized and extended. This system provides amplification of specific gene sequences and is suitable for simultaneous or sequential detection systems. O-grp-1 specific serotyping reactions are taught by Fitzgerald, C., et al., J. Clin. Microbiol., 2007; 45:3323-3334. It is appreciated that while the description herein is generally directed to gene sequences, that detection of mRNA that is at least a portion of a target gene transcription product is equally detectable by the processes and compositions of the inventions. As such, it is appreciated that the complements of all primers and probes described herein are similarly suitable in the invention.

The *Salmonella* nucleic acid sequences are optionally amplified before or simultaneous with being detected. The term "amplified" defines the process of making multiple copies of the nucleic acid from a single or lower copy number of nucleic acid sequence molecule. The amplification of nucleic acid sequences is carried out in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In some embodiments, the enzyme is hot-start iTaq DNA polymerase from Bio-rad (Hercules, Calif.). Suitable enzymes will facilitate combination of the nucleotides in the proper manner to form the primer extension products that are complementary to each mutant nucleotide strand. Generally, the synthesis is initiated at the 3'-end of each primer and proceeds in the 5'-direction along the template strand, until synthesis terminates, producing molecules of different lengths. There may be amplification agents, however, that initiate synthesis at the 5'-end and proceed in the other direction, using the same process as described above. In any event, the processes of the invention are not to be limited to the embodiments of amplification described herein.

One process of in vitro amplification, which is used according to this invention, is the polymerase chain reaction (PCR) described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain processes are known to those of skill in the art and may be used in the process of the invention. For example, DNA is placed in a reaction tube in a thermocycler along with supporting PCR reagents and subjected to a preheat step of 95° C. for 15 minutes, followed by 30 cycles of 94° C. for 30 seconds, 48° C. for 60 seconds, and 72° C. for 90 seconds, followed by a finishing cycle at 72° C. for 10 minutes.

In a non-limiting embodiment, a first stage assay is preformed using O-grp-1 primers and probes of the sequences of Table 1. The O-grp-1 primers and probes, as well as all other primers and probes listed herein are appreciated to include variants thereof, analogs thereof, derivatives thereof, or complements thereof. The terms primer or probe are used herein are appreciated to include envisioned variants, analogs, derivatives, and complements. Optionally in some embodiments, when the term primer or probe is used, it is limited to be directed to one or more primers or probes that are taught as having a sequence of any of SEQ ID NOs. 1-135 and excludes variants, analogues, or derivatives. It is appreciated that for Table 1 and all other tables that a corresponding forward primer and a reverse primer intended to amplify a single target sequence together are a primer set.

TABLE 1

| Name | Sequence (5'->3') | SEQ ID NO: |
|---|---|---|
| Forward Primers | | |
| A/D-F | GA GTT TAT ATG CAT ATA CTA A | 1 |
| B-F | GC ATA AAA CAT CAT CTC TCA TAA A | 2 |
| C1-F | GC TTT AAT CCA ATA TAA AA | 3 |
| C2-F | CA GAC GTT TGT TTT ATA A | 4 |
| E-F | CT GAT TTA ACC GGG TAT TAT TTA T | 5 |
| G-F | CT CTT GAT GAA TGT TAT TA | 6 |
| Reverse primers | | |
| A/D-R | TAC TGG TAA ACT TAT C | 7 |
| A/D-SubSpcII | TGC TGG TAA ATT TAT C | 8 |
| B-R | CGC ATA TGT TGA TAA TTA AAA TCT TT | 9 |
| C1-R | TAA ATA TAT GAT AGT TCC AAA TAA | 10 |
| C2-R | GAT CGT ACA ATC AAT ATC | 11 |
| E-R | CTT TTC TAT GCA GTG GTT TAA | 12 |
| G-R | GTT AAC CCC TCC TAA TA | 13 |
| Probes | | |
| A | GC GGC GGC GAA CTC ATT T | 14 |
| D | GC GGC GGC GAG TTC ATT T | 15 |
| D (subsp II) | GT GGC TGC GAG TTC ATT T | 16 |
| B | TT TAT TGC CAA ATC AAG AAC TTT AAT GGT TTT A | 17 |
| C1 | AT GAA ATG TCG ACG CAC ATA GAA TAA GAA TAA GC | 18 |
| C2 | TC CCT CTC ACC GTA AAC ATG TTC TAA ACG TAA ATT | 19 |
| E | AG GAT ATA TGT TAA GGC TGT ACT TAT ACC TAG CT | 20 |
| O:13 | AT ATA TAG ATG TTT ATT ATA TTT GCA TTC CCC A | 21 |

The O-grp-1 primers are optionally combined in separate reaction chambers or a single amplification reaction chamber and/or an amplification reaction set with primers for the H antigens of fliC and fljB. It is appreciated that each set of primers of O-grp-1 and set of primers of H-ag are optionally placed in a single reaction tube, divided between two reaction chambers with one for all sets of the O-grp-1 and a second for all the sets of the H-ag, or each set is optionally placed in an independent reaction tube. It is further appreciated that each of the O-grp-1 primer sets and H-ag primer sets may be used in simultaneous or non-simultaneous amplification reactions. In some embodiments, the amplification reaction conditions (e.g. buffers, polymerases, reagent concentrations, melting temperature and time, annealing temperature and time, extension temperature and time, among others) are optionally uniform for all primer sets within a first stage assay or subgroup thereof.

A first stage optionally includes examination of H-ag. Table 2 illustrates optional H antigen primers are probes. Throughout the description, the bold characters indicate the optional presence of a locked nucleotide, and the lowercase letters indicate a non-wild type base. It is appreciated that any primer or probe operable in the methods optionally include an insertion, deletion, or alternate base that is useful for improving the specificity of hybridizing to a target sequence. As such, an H-ag optionally includes those primers and probes listed in Table 2.

TABLE 2

| Name | Sequence (5'->3') | SEQ ID NO: |
|---|---|---|
| Forward Primers | | |
| 1EN_F1 | CGCTGAACGTGCAGAAAGAGTATGATGT | 22 |
| 1EN_F2 | AACGTGCAGAAAAAATATGATGT | 23 |
| ri_F | GTGCAACAAAAATATAAGGTCAGC | 24 |
| bd_F | GCGAACGACGGTGAAACTAT | 25 |
| G_F | TCCAGCTTCAAGAATGTTACGGG | 26 |
| z51_F | ATCTAATTTCAAAAACGTTACTGG | 27 |
| z29_F | AAAAAGCCTTGGAATGGATGG | 28 |
| Z4_F | AGCTGGGCTTAGATAAATTAGATGT | 29 |
| L_F | GCAGAAAAAATATGATGTGAAGAGC | 30 |
| Reverse primers | | |
| 1EN_R | AACTGCCTTCAATTGTCTTACC | 31 |
| ri_R | CACCCGCTGCTGTCAATG | 32 |
| b_R | CGGTCACCTCAACGAAGTAG | 33 |
| G_R | TATAAACATTTTTGCTTGATTGTAAGG | 34 |
| mt_R | TAGCAGTATATTCAGCTCCCATT | 35 |
| c_R | ATTTTATTCGTCAGCAGTTTTTTC | 36 |
| y_R | AACCGCCTTCAATTGTTTTACC | 37 |
| eh_R | CGTCAATAGATTTTCCATTTTTATC | 38 |
| z29_R | CCGCGTTAACAAATGACAGC | 39 |
| Z4_R | GGCAGATTCAAAACGGTTC | 40 |
| d_R | GCATAGCCACCATCAATAACC | 41 |
| Probes | | |
| a-1 | CCTTCGGCTACATTAAGCACT | 42 |
| a-2 | TCTACAACTGATACTGGTTC | 43 |
| b | TGCCTATACGCCAAAAGGTACC | 44 |
| c | CTGGCGCAGCTAGCTTGAAAG | 45 |
| d | ACTACAAAGAAAGTTAATATTGATAC | 46 |
| j | ACTGGCGCCGATAAGGAC | 47 |
| e, h | GGCGATTCCTTGTCTGCTACG | 48 |
| i | TTGATAAGACGAACGGTGAGGT | 49 |
| k | ATGGTTTCCTTAAAGTTGACGTTAATAC | 50 |
| r | GGCACACCAACAGGACCAAT | 51 |
| z10 | AACCAACGAATGCAGTTGAA | 52 |
| z | CAATTGGGGCCTCGACTACTA | 53 |
| z35 | TGCTAAGAGCGGTTACTATAA | 54 |
| z29 | TGGCGCGCACAAAGCAAC | 55 |
| z6 | TTACAGACCCAGAAATTGCTG | 56 |
| Y | AAGCACTACGATGCCTACTGC | 57 |
| L-comp | AAAAGGCCAATTAGTTACGAT | 58 |
| v | AATGCCGACAACCACtGAAAG | 59 |
| z28 | AACCGCCGCGAAAGTGACA | 60 |
| EN-comp-1 | CACTGTAAGTGGTTATAC | 61 |
| EN-comp-2 | CACTGTAGGTGGTTATACCGATGC | 62 |
| x | ATATTATTCCACTGTAAGTGtGTTATACC | 63 |
| z15 | CTGTAGGTGtGTTATACCGATGC | 64 |
| 1-comp | CAATAATGGTACTACACTGGATGTAT | 65 |
| 2 | GTGtGTACGAATAGTACtGGC | 66 |
| 5-1 | GTGGTACGACTGGTACGGC | 67 |
| 6 | GTACGCTTGGCACGGCTTCTGTAA | 68 |
| 7 | CGAATGGTGCACCTAGTGTAACAGGTA | 69 |
| G-comp | ACGGTAATGGTACGGTTTCTACTAC | 70 |
| f | CGGtCGAATGTTGATGCTCGCTAC | 71 |
| m/g, m | TATTGCCACTGGCGCGAC | 72 |
| m/g, t | GTTTATACTTCCGTTGTAAGCGGTC | 73 |
| P | TGATATTGCCATTGGCGCTGGCG | 74 |
| s | CTGCGGTTAACCTATTCAtAGACGACTA | 75 |
| t-1 | GCTCCAACTGTTCCTGATAAAGTATACGTA | 76 |
| z51 | TATTAATTCTGGAGCAGTAACTGATGA | 77 |
| Z4-comp | ACCGAGCTGGGCTTAGATAAAT | 78 |
| z24 | GCTACCGTAGATAATAGTACTGGG | 79 |
| Iw_6_53 | TACCTCAATACCGCTGGTCTTAAT | 80 |
| t_21_8t | ATGAAGGTAATGtGTACGGTTTCTAC | 81 |
| z23-2 | CAGCTGATTTCGATAACGCAAAA | 82 |

The primers used to amplify the H-antigen regions are optionally targeted to a variable region of the gene. The primers used are designed to amplify sequences from all known H antigens in a multiplex assay format. Thus, a single reaction chamber is optionally used wherein all the primers listed in Table 2 are combined to form a plurality of amplification products representative of the entire H-antigen composition of the sample. The identification of H-antigen is then obtained by identification of the probes that hybridize to the specific amplification products. Thus, the H-antigen portion of a first stage assay is optionally a multiplex assay designed to amplify all known sequences of H-antigen with the identification obtained by identification of probe hybridized to an amplification product.

In some embodiments, a second stage assay is included to determine whether a sample contains a *Salmonella* serotype that is not detectable by the first stage assay. A second stage assay optionally detects the presence and serotype of a *Salmonella* in the sample. A second stage assay optionally is performed simultaneous with, prior to, or subsequent to a first stage assay. A second stage assay is used to detect O-grp-2 targets, a single serotype illustratively *Salmonella* ser. Enteritidis, additional targets, or species and subspecies targets. It is appreciated that the tenon "second stage assay" is meant to discern an additional or simultaneous assay when used in conjunction with the compositions or processes of a first stage assay. It is further appreciated that any second stage assay is operable independent of a first stage assay and when referred for use independent of a prior assay is referred to herein as a first stage assay or by the specific target or set of targets identifiable by the assay.

A second stage assay is optionally operable to detect additional targets that include sequences of the genes encoding Sdf, Vi, and FljB. Illustrative primers and probes for detection and serotyping additional targets are listed in Table 3.

TABLE 3

| Original name | Name | Sequence (5'->3') | SEQ ID NO: |
|---|---|---|---|
| Forward Primers | | | |
| sdfF | sdf1_F | GTG GTG GCT GGC GAA TGG | 83 |
| via_FTr | viaB_F | AGGTTATTTCAGCATAAGGAGACTT | 84 |
| fljB F2 | fljB_F | CCTGGATGACACAGGTAAGCC | 85 |
| Reverse Primers | | | |
| sdfR | sdf_R | GGA GAG GCG GTT TGA TGT GG | 86 |
| via_RTr | viaB_R | CTCTTCCATACCACTTTCCGA | 87 |
| fljB R2 | fljB_R | TGGGTCAGCAGCGACAGA | 88 |

| Probes | | Sequence | |
|---|---|---|---|
| sdf1_1 | sdf1 | TA CTC CCT GAA TCT GAG AAA | 89 |
| VI1_1 | viaB | GACGGAGCAGAGAGATTATCG | 90 |
| fljB1_14 | fljB | ATAACATTGGTTATCAAAAA CCTTCCAAAA | 91 |

In some embodiments a second stage O-grp-2 assay is performed. An O-grp-2 assay is used along with a first stage assay to collectively detect and serotype 99% of *Salmonella* that could be present in a sample. An O-grp-2 assay optionally uses primers and probes as listed in Table 4.

TABLE 4

| Name | Sequence (5'->3') | SEQ ID NO: |
|---|---|---|
| Forward Primers | | |
| O35-F | AGA GGA ATA AAA AAT TTT ACG TTG T3 | 92 |
| O50-F | GCA TGG ATG GGT GGA ATT AGT3 | 93 |
| O614-F | ATT GTT GCA TTT GTA AAA TGT AT3 | 94 |
| O11-F | CGA TGG TCC ATT ATT TGA TTC TT3 | 95 |
| O16-F | ATA ATC CTG AAA ATG GTA TAA CT3 | 96 |
| Reverse primers | | |
| O35-R | ATT GTT TTC CTT AAA TTA ATC CTC A | 97 |
| O50-R | GAG CCA TGC CCA TAT CAG C | 98 |
| O614-R | AAC ACC ATG CAT CTT AAC TAA | 99 |
| O11-R | GGG GAA GAC CTT CAG ATA AAG A | 100 |
| O16-R | ATG TTT CGC CAT ATA AAA TAT GA | 101 |
| Probes | | |
| O35 | GAA TCT GTC CTC TGT AAC TTA TTA ATA ATG ATT G | 131 |
| O50 | CCA AGT ATA TGC AGA TAA TAG GGT AAA ATC AGA AT | 132 |
| O6, 14 | GAC ATA TGA GAT ATA CAA ACC TAT TTT ATA ATA CCC TTG | 133 |
| O11 | CCT GTA AAA ATA TAC CTA TTG TCT ATA AAA TAG CTC TT | 134 |
| O16 | ATT ATT GTA AAT TGC CAT TTA AAC ACT TTT TTA GC | 135 |

In some embodiments, a single *Salmonella* serotype is screened, detected, or serotyped. Optionally, a method is targeted to serotype specific detection, illustratively detection of *Salmonella* ser. Enteritidis. *Salmonella* ser. Enteritidis exposure may lead to severe illness and even death. Exposure to *Salmonella* ser. Enteritidis is most commonly from consuming contaminated poultry or eggs. A chicken harboring *Salmonella* ser. Enteritidis can pass the bacteria to the eggs. Thus, an assay that can quickly and specifically detect *Salmonella* ser. Enteritidis in a sample that is derived from a chicken, or other sample, is desirable. A method of serotype specific detection of *Salmonella* ser. Enteritidis (SE Assay) optionally includes primers and probes that will specifically amplify and detect target gene sequences. Illustrative examples of primers and probes include those listed in Table 5, with an F or a R indicating a forward or reverse primer respectively.

TABLE 5

| Original name | Name | Sequence (5'->3') | SEQ. ID NO: |
|---|---|---|---|
| Primers | | | |
| invAF1 | invAF1 | CTGCTTTCTCTACTTAACAGTGCTCG | 107 |
| InvAR3 | InvAR3 | CGCATCAATAATACCGGCCTTC | 108 |
| PhoSspF2 | PhoSspF2 | ATGATGCGCGTACTGGTTGTAG | 109 |
| PhoSspR2 | PhoSspR2 | TTTGATGACCTCTTCATTGACGGATAA | 110 |
| | A/D-F | GA GTT TAT ATG CAT ATA CTA A | 111 |
| | A/D-R | TAC TGG TAA ACT TAT C | 112 |
| G-F3 | G_F | TCCAGCTTCAAGAATGTTACGGG | 113 |
| G-Rev2 | G_R | TATAAACATTTTTGCTTGATTGTAAGG | 114 |
| sdfF | sdf1_F | GTGGTGGCTGGCGAATGG | 115 |
| sdfR | sdf_R | GGAGAGGCGGTTTGATGTGG | 116 |
| Probes | | | |
| invA_3 | invA_3 | CCTGGCGGTGGGTTTTGTTGTCTTC | 117 |
| phoP | phoP | TCCAGGATTCAGGTCACCA | 118 |

TABLE 5-continued

| Original name | Name | Sequence (5'->3') | SEQ. ID NO: |
|---|---|---|---|
| SspI | SspI D | CCTTAATGAACACCTTCC GC GGC GGC GAG TTC ATT T | 119 120 |
| G_20 | G-comp | ACGGTAATGGTACGGTTTCTACTAC | 121 |
| gm_1_2_2 | m/g, m | TATTGCCACTGGCGCGAC | 122 |
| sdf_1 | sdf1 | TA CTC CCT GAA TCT GAG AAA | 123 |

In some embodiments, a species and subspecies assay is used along with a first stage assay, a second stage assay, an SE assay, combinations of assays, or independent of other assays. The subspecies assay is capable of detecting up to all species and subspecies of *Salmonella*. The species and subspecies assay optionally uses a single forward and reverse primer pair to amplify a single gene sequence. The species and subspecies assay optionally uses two pairs of primers to amplify the gene sequence in overlapping regions from multiple serotypes. The specificity of the assay is optionally achieved by the use of species and subspecies specific probes. Illustrative examples of primers and probes used in a species and subspecies assay are listed in Table 6. The lowercase letters indicate a non-wild type base.

TABLE 6

| Original name | Name | Sequence (5'->3') | SEQ ID NO: |
|---|---|---|---|
| Primers | | | |
| invAF1 | invAF1 | CTGCTTTCTCTACTTAACAGTGCTCG | 107 |
| InvAR3 | InvAR3 | CGCATCAATAATACCGGCCTTC | 108 |
| Pho Ssp F2 | Pho Ssp F2 | ATGATGCGCGTACTGGTTGTAG | 109 |
| Pho Ssp R2 | Pho Ssp R2 | TTTGATGACCTCTTCATTGACGGATAA | 110 |
| Probes | | | |
| invA_3 | invA_3 | CCTGGCGGTGGGTTTTGTTGTCTTC | 117 |
| phoP | phoP | TCCAGGATTCAGGTCACCA | 118 |
| I_1 | I_1 | TACCTTAATGAACACCTTCC | 124 |
| II_1_3 | II_1_3 | GGCCTGTCCTTAATACG | 125 |
| IIIa1_8 | IIIa1_8 | TGACGTTTTACTACCGGTTCTG | 126 |
| IIIb1_4 | IIIb1_4 | TGCCAGTGCTGGTGTTAACCG | 127 |
| IV_5, | IV_5, | TCGATGCAGCAGAAGATGCC | 128 |
| VI5tt_2 | VI5tt_2 | GGCAAGATAAAGTCtGtAGGTT | 129 |
| V3_18 | V3_18 | GAGCATCGCCGGACATCGCGATTG | 130 |

It is appreciated that the primers and probes described herein are optionally mixed and matched to form custom blends for specific desired circumstances of the user. Illustratively, custom kits can be arranged for investigation of a particular serotype or groups of serotypes, the source of an outbreak, in research projects with particular desired outcomes or testing particular hypotheses, or other desired use.

A primer, probe, or combinations thereof, optionally include one or more labels. A label optionally allows a user to distinguish an amplification product from other amplification products or to bind to a particle or detect whether an amplification product is affixed to a particle. A label is illustratively a fluorophore such as fluorescein (FAM), a radioactive label, or a specific binding pa1 tiler such as streptavidin or biotin. A forward or a reverse primer is optionally labeled. In some embodiments, both a forward and reverse primer are labeled. The presence, type, requirement, or absence of a label is determined by a user depending on the method used for detection of specific amplification products. Illustratively, reverse primers are labeled with streptavidin for subsequent association with a biotinylated fluorophore optionally for detection in a Luminex multiplex assay system. Optionally, a forward or reverse primer or a probe is labeled with biotin for interaction with a streptavidin bound fluorophore such as a bead for use in a Luminex based assay system.

When a Luminex assay system is used, particles are associated with a probe specific for a nucleotide sequence of a single serotype or subspecies. The size, type, and composition of the particles are illustratively described in U.S. Pat. No. 6,649,414. It is appreciated that each serotype or subspecies specific probe is associated with a particle type that is distinguishable from the particle type associated with probes specific for different serotypes or subspecies. Illustratively, the O-grp-1 probes are each associatable or associated with a unique particle that has a unique fluorescence signature. The H-ag probes are optionally associated with yet additional unique particles each with unique fluorescence signatures. Thus, an assay includes a detection phase whereby the presence of an amplicon bound to a probe is detectable by detecting the label on the primer and the identity of the amplicon is determined by detecting the specific fluorescence signature of the particle to which the probe is associated.

An oligonucleotide probe, as an exemplary amplicon specific detection agent, is illustratively associated with a particle via a covalent bond. Methods of attaching probes to particles are described by Fitzgerald, C. et al., J Clin Microbiol, 2007; 45:3323-34. It is appreciated that other methods of associating (covalently or non-covalently) nucleotide primers or probes with a support are known in the art and included herein. The individually labeled beads are optionally pooled in to groups for specific detection of a plurality of serotypes in a single detection phase. Optionally, in a first stage assay probes for each of the O-grp-1 serotypes and H-ag serotypes are pooled and incubated with the reaction products from the amplification phase of the first stage.

In some embodiments, a forward or reverse primer includes a biotin label. A label is optionally present on or near a 3' or 5' end of a primer or probe. Following hybridization of the microspheres with any amplification product, the detection mixture is combined with a detection buffer that includes a fluorophore or other label conjugated to streptavidin or other specific binding partner. The tight interaction between biotin and streptavidin (typically with dissociation constants in the femtomolar range) allows direction of the streptavidin-fluorophore to labeled amplification products. In other embodiments, an amplification product is directly labeled with a fluorophore such that a secondary association with a fluorophore is not necessary. The fluorescent label on an amplification product is distinguishable from the fluorescent signals of the particles such that identification of which beads have probes hybridized to the amplification product can be detected and identification of the particular probe hybridized to an amplification product is determined by identification of the particle through its unique fluorescence signature.

Identification of a particle with a probe hybridized to an amplification product is illustratively performed on a flow cytometer. An illustrative example includes the Luminex 100 or Luminex 200 systems available from Luminex Corp., Austin, Tex.

In some embodiments, a real-time PCR reaction such is used to detect the presence of a specific amplification product. A fluorescent reporter dye, such as FAM dye (illustratively 6-carboxyfluorescein), is optionally covalently linked to the 5' end of the oligonucleotide primer or probe. Other dyes illustratively include TAMRA, AlexaFluor dyes illustratively include AlexaFluor 495 or 590, Cascade Blue, Marina Blue, Pacific Blue, Oregon Green, Rhodamine, Fluoroscein, TET, HEX, Cy5, Cy3, and Tetramethylrhodamine. Each of the reporters is quenched by a dye at the 3' end or other non-fluorescent quencher. When processes such as real-time PCR are used to detect amplification products, quenching molecules are included with a label on a probe that are suitably matched to the fluorescence maximum of the dye. In some embodiments, a 6-carboxyfluorescein reporter dye is present at the 5'-end and matched to Black Hole Quencher (BHQ1, Biosearch Technologies, Inc., Novato, Calif.) The fluorescence signals from these reactions are captured at the end of extension steps as PCR product is generated over a range of the thermal cycles, thereby allowing the quantitative determination of the viral load in the sample based on an amplification plot.

The primers and probes for use in amplifying the nucleic acid sequences of Salmonella may be prepared using any suitable process, such as conventional phosphotriester and phosphodiester processes known in the art or automated embodiments thereof so long as the primers and probes are capable of hybridizing to the nucleic acid sequences of interest. One process for synthesizing oligonucleotides on a modified solid support is described in U.S. Pat. No. 4,458,066. The exact length of primer will depend on many factors, including temperature, buffer, and nucleotide composition. The primer must prime the synthesis of extension products in the presence of the inducing agent for amplification.

Primers sets are complementary to a portion of each strand of nucleotide sequence to be amplified. Probes are complementary to nucleotide sequences that are useful for identifying an amplification product indicative illustratively of a serotype or subspecies. The term "complementary" means that the primer hybridize with their respective strands under conditions that allow the agent for polymerization to function, or a probe will hybridize with an amplification product under conditions that allow for detection of the hybridization. In other words, the primers that are complementary to the flanking sequences hybridize with the flanking sequences and permit amplification of the nucleotide sequence. Optionally, the 3' terminus of the primer that is extended is perfectly base paired with the complementary flanking strand. Probes optionally possess nucleotide sequences complementary to one or more strands of the amplification product.

Those of ordinary skill in the art will know of various amplification processes that can also be utilized to increase the copy number of target Salmonella nucleic acid sequence. The nucleic acid sequences detected in the process of the invention are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., Bio-Technology 3:1008 1012 (1985)), allele-specific oligonucleotide (ASO) probe analysis (Conner et al., PNAS 80: 278 (1983)), oligonucleotide ligation assays (OLAs) (Landegren et al., Science 241:1077 (1988)), RNase Protection Assay and the like. Molecular techniques for DNA analysis have been reviewed (Landegren et al, Science 242:229 237 (1988)). Following DNA amplification, the reaction product may be detected by Southern blot analysis, with or without using radioactive probes. In such a process, for example, a small sample of DNA containing the nucleic acid sequence obtained from the tissue or subject is amplified, and analyzed via a Southern blotting technique. The use of non-radioactive probes or labels is facilitated by the high level of the amplified signal. In some embodiments of the invention, one nucleoside triphosphate is radioactively labeled, thereby allowing direct visualization of the amplification product by autoradiography. In some embodiments, amplification primers are fluorescently labeled and run through an electrophoresis system. Visualization of amplified products is optionally by light detection followed by computer assisted graphic display, without a radioactive signal.

Other methods of detection amplification products illustratively include gel electrophoresis, mass spectrometry, liquid chromatography, fluorescence, luminescence, gel mobility shift assay, fluorescence resonance energy transfer, nucleotide sequencing, enzyme-linked immunoadsorbent assay, affinity chromatography, chromatography, immunoenzymatic methods (Ortiz, A and Ritter, E, Nucleic Acids Res., 1996; 24:3280-3281), streptavidin-conjugated enzymes, DNA branch migration (Lishanski, A, et al., Nucleic Acids Res., 2000; 28(9):e42), enzyme digestion (U.S. Pat. No. 5,580,730), colorimetric methods (Lee, K., Biotechnology Letters, 2003; 25:1739-1742), or combinations thereof.

The term "labeled" with regard to the primer or probe is intended to encompass direct labeling of by coupling (i.e., physically linking) a detectable substance to the probe, as well as indirect labeling of the probe by reactivity with another reagent that is directly labeled. Examples of indirect labeling include detection of a probe or primer using a fluorescently labeled antibody and end-labeling or centrally labeling of a primer or probe with biotin such that it can be detected with fluorescently labeled streptavidin. The detection method of the invention can be used to detect RNA (particularly mRNA) or genomic nucleic acid in a sample. For example, in vitro techniques for detection of nucleic acid include northern hybridizations, in situ hybridizations, reverse transcription-PCR, real-time-PCR, and DNase protection. In vivo techniques for detection of Salmonella include introducing into a subject organism a labeled antibody directed against a polypeptide component or directed against a target nucleic acid sequence. For example, the antibody can be labeled with a radioactive marker whose presence and location in the subject organism can be detected by standard imaging techniques, including autoradiography.

The size of the primers or probes used to amplify a portion of the nucleic acid sequence and detect an amplification product of Salmonella is at least 5, and often at least or up to 10, 15, 20, 25, 30, 35, or 40 nucleotides in length. In some embodiments, a probe is 40 nucleotides or fewer in length. A probe is optionally 40, 39, 38, 37, 36, 35, 34, 33, or fewer nucleotides. A probes is optionally from 30 to 45 nucleotides in length or any value or range therebetween. It is appreciated that any length there between may be used depending on the desired characteristics of the primer or probe. A probe optionally includes a nucleotide sequence and a label. Optionally, the GC ratio is above 30%, 35%, 40%, 45%, 50%, 55%, or 60% so as to prevent hair-pin structure. The amplicon is optionally of sufficient length to be detected by standard molecular biology methodologies. The forward primer is optionally shorter than the reverse primer or vice versa. Techniques for modifying the Tm of either primer are operable herein. A primer or probe optionally includes LNA-dA or LNA-dT (Exiqon, Inc., Wobrun, Mass.) optionally to match Tm with a corresponding alternate primer or with other probes used in a detection phase.

An inventive process optionally uses a polymerization reaction that employs a nucleic acid polymerizing enzyme, illustratively a DNA polymerase, RNA polymerase, reverse transcriptase, or mixtures thereof. It is further appreciated under such circumstances that accessory proteins or molecules are present to form the replication machinery. A polymerizing enzyme is optionally a thermostable polymerase or thermo-degradable polymerase. Use of thermostable polymerases is well known in the art such as Taq polymerase available from Invitrogen Corporation, Carlsbad, Calif. Thermostable polymerases allow a polymerization reaction to be initiated or shut down by changing the temperature other condition in the reaction mixture without destroying activity of the polymerase.

Accuracy of the base pairing of DNA sequence amplification is provided by the specificity of the enzyme. Error rates for Taq polymerase tend to be false base incorporation of 10-5 or less. (Johnson, Annual Reviews of Biochemistry, 1993: 62:685-713; Kunkel, Journal of Biological Chemistry, 1992; 267:18251-18254). Specific examples of thermostable polymerases illustratively include those isolated from *Thermus aquaticus, Thermus thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The polymerases are optionally bound to a primer. When the target gene sequence is a single-stranded DNA molecule due to heat denaturing, the polymerase is bound at the primed end of the single-stranded nucleic acid at an origin of replication. A binding site for a suitable polymerase is optionally created by an accessory protein or by any primed single-stranded nucleic acid.

In some embodiments, detection of amplification products of O-grp-1, O-grp-2, H-ag, SE, or other target nucleic acid sequence is achieved by mass spectrometry. Mass spectrometry can be used to simultaneously detect the presence of *Salmonella* and decipher mutations in target nucleic acid sequences allowing identification and monitoring of emerging strains. Further, mass spectrometers are prevalent in the clinical laboratory. Similar to fluorescence based detection systems, mass spectrometry is capable of simultaneously detecting multiple amplification products for a multiplexed and controlled approach to accurately quantifying components of biological or environmental samples.

Multiple mass spectrometry platforms are suitable for use in the invention illustratively including matrix assisted laser desorption ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (UPLC-ID/MS/MS), and variations thereof.

Optionally, multiple amplification products are simultaneously produced in a PCR reaction that is then available for simultaneous detection and optional quantification. Optionally, a single sample is subjected to analysis for the simultaneous or sequential detection of *Salmonella* genetic sequences. Oligonucleotide matched primers are simultaneously or sequentially added and the biological sample, or a portion thereof, is subjected to proper thermocycling reaction parameters. For detection by mass spectrometry or Luminex based detection systems, the amplification products may be combined in a single sample and are simultaneously analyzed allowing for rapid and accurate determination of the presence of Salmonella. Optionally, analysis by real-time PCR is employed capitalizing on multiple probes with unique fluorescent signatures. Thus, each target sequence is detected without interference by other amplification products. Optionally, a Luminex multiplex based detection system is used to detect the presence of particular amplification products. This, multi-target approach increases confidence in quantification and provides for additional internal control.

In some embodiments, the processes further involve obtaining a control sample from a control subject or from an environment known not to have *Salmonella* therein or to have a known *Salmonella* serotype, contacting the control sample with a compound or agent capable of detecting the presence of serotype specific *Salmonella* nucleic acids in the sample, and comparing the presence or absence of target nucleotide sequences in the control sample with the presence or absence target sequences in the test sample.

The inventions also encompass kits for detecting the presence of *Salmonella* nucleic acids in a test sample. A kit, for example, includes a primer or plurality of primers, probe or plurality of probes, or combinations thereof, and optionally labeled, capable of producing and detecting an amplification product in a test sample and, in certain embodiments, for determining the quantity of *Salmonella* target sequence in the sample.

For oligonucleotide-based kits, the kit includes, for example: (1) oligonucleotide probe, optionally a detectably labeled oligonucleotide probe, which hybridizes to an amplification product sequence of *Salmonella* and/or (2) a pair of primers (one forward and one reverse, optionally labeled) useful for amplifying a target sequence containing at least a portion the *Salmonella* sequence of interest. The kit can also include, e.g., a buffering agent, a preservative, or a protein stabilizing agent. The kit can also include components necessary for detecting the probe (e.g., a particle or other support). The kit can also contain a control sample or a series of control samples that is assayed and compared to the test sample contained. Each component of the kit is optionally enclosed within an individual container and all of the various containers are usually enclosed within a single package along with instructions for use.

Inventive methods herein are amenable to use for diagnosis of *Salmonella* infection in a subject capable of infection by or with *Salmonella*.

To increase confidence and to serve as an internal or external control, a purified solution containing one or more *Salmonella* serotypes is used as a sample. By amplification of a single sample with known quantities of *Salmonella* or of a set of samples representing a titration of *Salmonella*, the level of *Salmonella* in the unknown sample is determined. Optionally, the purified and quantified *Salmonella* solution is analyzed in parallel with the unknown sample to reduce inter assay error or to serve as a standard curve for quantitation of unknown *Salmonella* in the sample. Using purified and quantified *Salmonella* solution provides for a similar complete genetic base DNA strand for amplification.

EXAMPLES

Example 1

DNA Sequences

The sequences of the H antigens fliC and fljB utilized for assay design are from McQuiston, J, et al., J Clin Microbiol, 2004; 42:1923-32. Additional sequencing of fliC and fljB is performed as described McQuiston, J, et al., J Bacterial, 2008; 190:7060-7. All sequences were submitted to GenBank under accession numbers HM141979-HM142068.

Sequencing of the O antigen genes of the rfb gene cluster of O:13 are performed as described by Fitzgerald, C. et al., J. Clin. Microbiol., 2007; 45: 3323-3334. Briefly, The *Salmonella* serogroup O13 rfb region is amplified by PCR using the Expand Long PCR kit (Roche) according to the manufacturer's instructions. Oligonucleotide primers are used that correspond to the middle of the JUMPstart sequence and the 5' end of gnd, as previously described by Li and Reeves, Microbiology, 2000; 146:2291-2307. Overall, both primer walking and subcloning were performed until the entire sequence of the rfb region was obtained. Sequencing reactions were performed on a Perkin-Elmer Applied Biosystems 377 automated DNA sequencer using the BigDye Terminator cycle sequencing ready reaction mix according to the manufacturer's instructions (Perkin-Elmer Applied Biosystems, Foster City, Calif.).

Example 2

Primer and Probe Design and Evaluation

For the H antigens, alignment of closely related fliC and fljB allele sequences and deduced protein sequences identified conserved nucleotide substitutions or amino acid residues corresponding to the antigen type. Similar procedures are performed for the rfb gene cluster (FIG. 1).

Probe and primer design were done using Visual OMP software (DNAsoftware Inc., Ann Arbor, Mich.). The software was also used for experimental simulation to evaluate cross reactivity, probe binding specificity and hairpin formation in silico. The sequences obtained for the H antigens and the O antigen rfb gene sequences are used as source gene sequences.

The primers are optimized for positive signal intensity on the Bio-plex platform and adjusted to produce amplification products that are between 90 bp to 420 bp long and typically from 122 bp to 150 bp long. The H antigen probes were designed to a common DNA sequence for all antigens of that type within the variable region of the coding sequence that was distinct from other antigen types. Probe hybridization was evaluated at different temperatures (37° C., 52° C., 53° C.), and the fluorescence signal intensity and stringency of hybridization were found to be optimal at a hybridization temperature of 52° C.

Probes with a median fluorescent intensity (P/N ratio >6.0) when hybridized to the allele of the respective antigen type and without cross reactivity to other closely related antigen types were evaluated against panels of increasing genetic diversity. Each probe was first demonstrated to result in a positive signal for five serotypes with like antigens and up to 16 serotypes which should be negative but are genetically related. If successful in these preliminary evaluations, each probe was tested against all serotypes of like antigens and genetically related antigens in the Top 100 serotypes. If results of this panel were successful, the probe was added to the assay and was evaluated against the panel of 500 isolates as a complete set of probes.

The primers and probes for the O-grp-1 targets are presented in Table 1. The primers and probes for the O-grp-2 targets are presented in Table 4. The primers for the H-ag targets are presented in Table 2.

For oligonucleotide probes directed to related alleles, several methods were employed to increase specificity while maintaining high signal strength. To reduce cross reaction within a specific region of a nucleic oligonucleotide probe, a thymine base was introduced within four bases of the target substitution (e.g. H: 2; f; m/g,m; p; s; v; x; and z15). Locked nucleic acid (LNA) bases were incorporated into two probes (e.g. H:2 and m/m,t) to increase the hybridization efficiency of the probe.

Figure 2A:
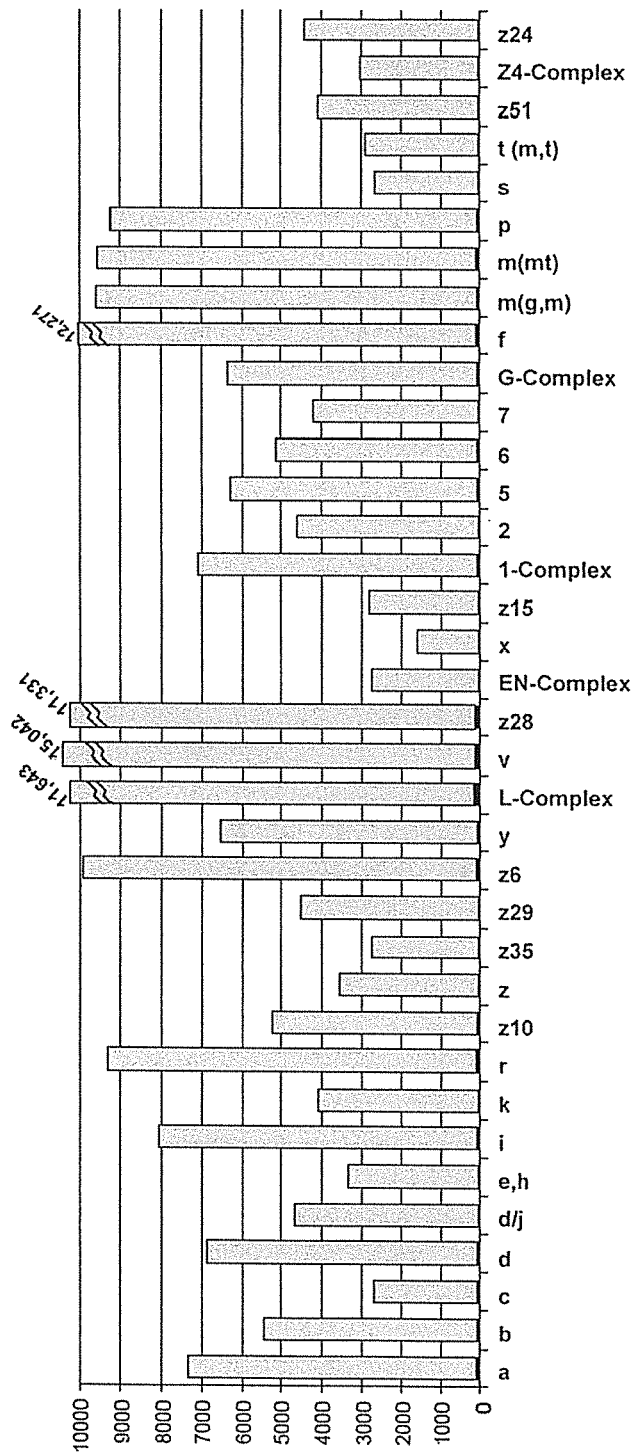
FIGS. 2A and 2B illustrate the average signal strength of each probe from five isolates expressing the 2 immunologically defined antigens (FIG. 2A); and the corresponding average P/N ratio data for each of the probes (FIG. 2B)
Figure 2B:
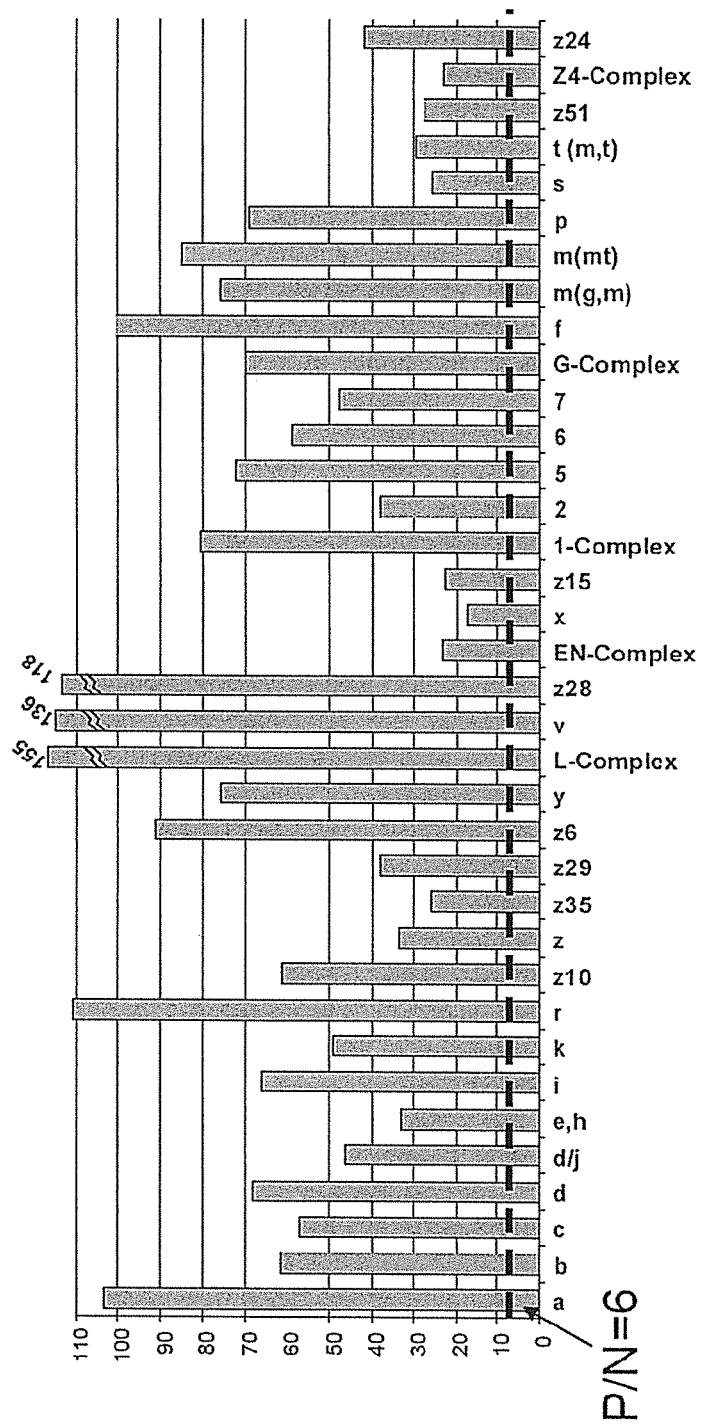

The H-ag probes have average MFI values ranging from a low of 1,596 (H:x) to a high of 15,042 1 (H:v). The average signal strength of each probe from five isolates expressing the 2 immunologically defined antigens is reported in FIG. 2A. The corresponding average P/N ratio data for each of the probes is shown in FIG. 2B. The average background signal in the probes for this assay ranged from 46 to 148 on the high sensitivity setting of the Cal2 calibration of the Luminex instrument.

Example 3

Coupling Probes to Fluorescent Particles

DNA oligonucleotide probes of each group (O-grp-1, O-grp-2, H-ag, additional targets, SE, and subspecies) were synthesized with a 5' amino-linked carbon spacer arm. These were coupled to the carboxylated microsphere polystyrene microspheres (Luminex, Austin, Tex.) following the procedure described in Fitzgerald et. al., J. Clin. Microbiol., 2007; 45: 3323-3334. In brief, 2.5×106 microspheres were carbodiimide coupled with 200 pmol of oligonucleotide probe using freshly prepared 30 g/ml N-(3-dimethylaminodipropyl)-N-ethylcarbodiimide (EDC) (Pierce Chemicals, Ill.). The mixtures were incubated twice for 30 minutes at room temperature with 1 µl of freshly prepared EDC added at each 30 minute interval. Following coupling, the microspheres were centrifuged for 1 minute at 9,000×g and washed with 1.0 ml of 0.02% Tween-20 (Sigma, St. Louis, Mo.), followed by a second wash with 0.5 ml of 0.1% sodium dodecyl sulfate (Sigma, St. Louis, Mo.). The microspheres were then suspended in 50 µl of TE buffer (0.01M Tris-EDTA, pH 8.0, Sigma, St. Louis, Mo.) and stored at 4° C. in the dark. Individual microspheres coupled to probes were stored in TE at a concentration of approximately 250 microspheres/µl. Labeled beads were pooled into appropriate microsphere sets corresponding to the complement of antigens desired to be detected.

Example 4

Assay

A molecular serotyping assay is divided into two phases. The amplification phase involves using PCR based techniques to increase the copy number of target and include a label. A detection phase then involves hybridizing amplified target to probes and determining the identity of the amplified target.

Isolates were obtained from the CDC collection. Isolates were grown overnight on trypticase soy agar or in 1 ml Luria Broth (LB). DNA was extracted with Qiamp DNAeasy Kit (Qiagen, Valencia, Calif. USA) or Instagene Matrix (BioRad, La Jolla, Calif.) following manufacturer protocols, except that incubation times were reduced to 4 minutes at 55° C. followed by 4 minutes at 96-100° C. Genomic DNA preparations were quantified by spectrophotometry at A260/280 and diluted to 200 ng per ml before use.

Figure 3:
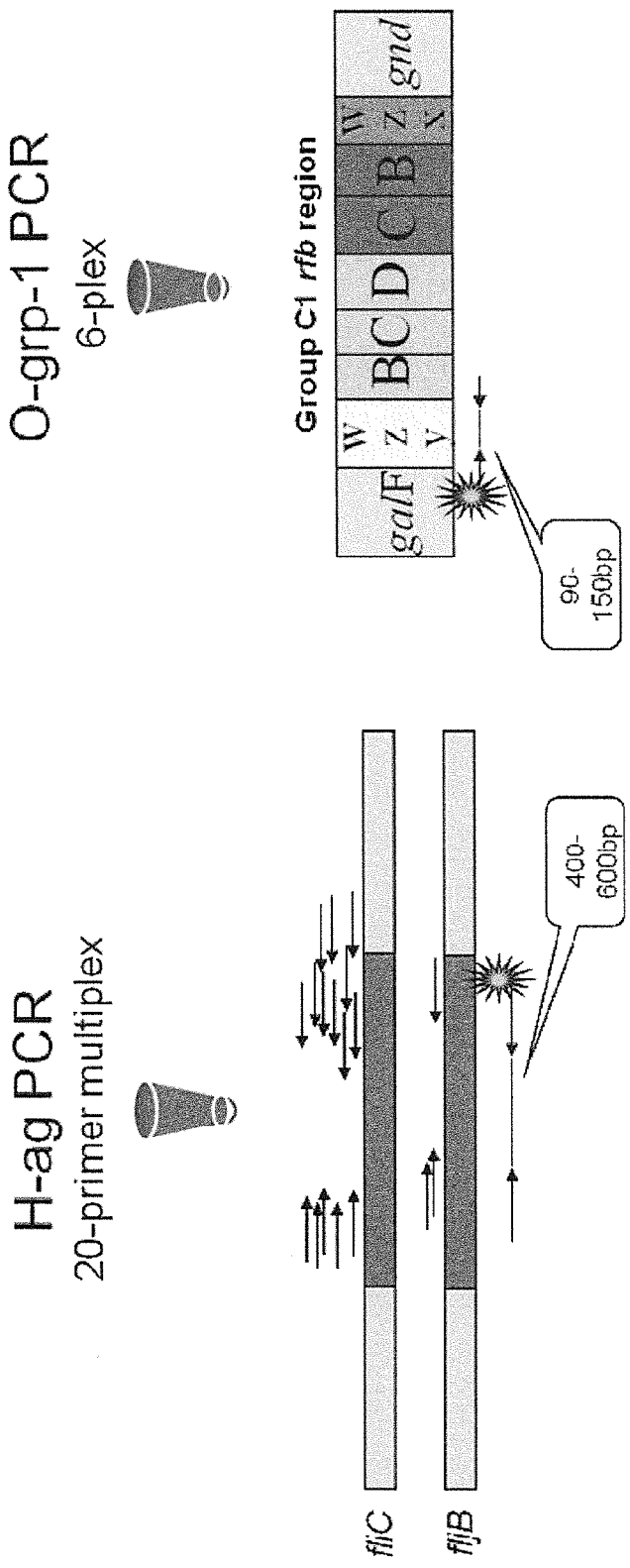
FIG. 3 is a schematic of the parallel amplification reactions according to one embodiment.

The amplification phase involves pooling primers (Table 1) that will amplify targets from O-grp-1 for a first amplification reaction and pooling the primers that will amplify targets from the H-ag (Table 2) for a second amplification reaction. Both the O-grp-1 amplification reaction and H-ag amplification reaction are performed simultaneously under identical conditions. The forward O-grp-1 primers and reverse H-ag primers are biotinylated at the 3' ends. A five-fold excess concentration of biotinylated primer is used relative to the unlabeled primer. PCR amplification is performed in 25 μl volumes using a Hot Start PCR kit (Promega, Madison, Wis.) according to the manufacturer's instructions with the following parameters: initial denaturation at 95° C. for 15 min; then 30 cycles of 94° C. for 30 s (denaturation), 48° C. for 60 s (annealing), and 72° C. for 90 s (extension); and 72° C. for 10 min (final extension). FIG. 3 is a schematic of the parallel amplification reactions.

Figure 4:
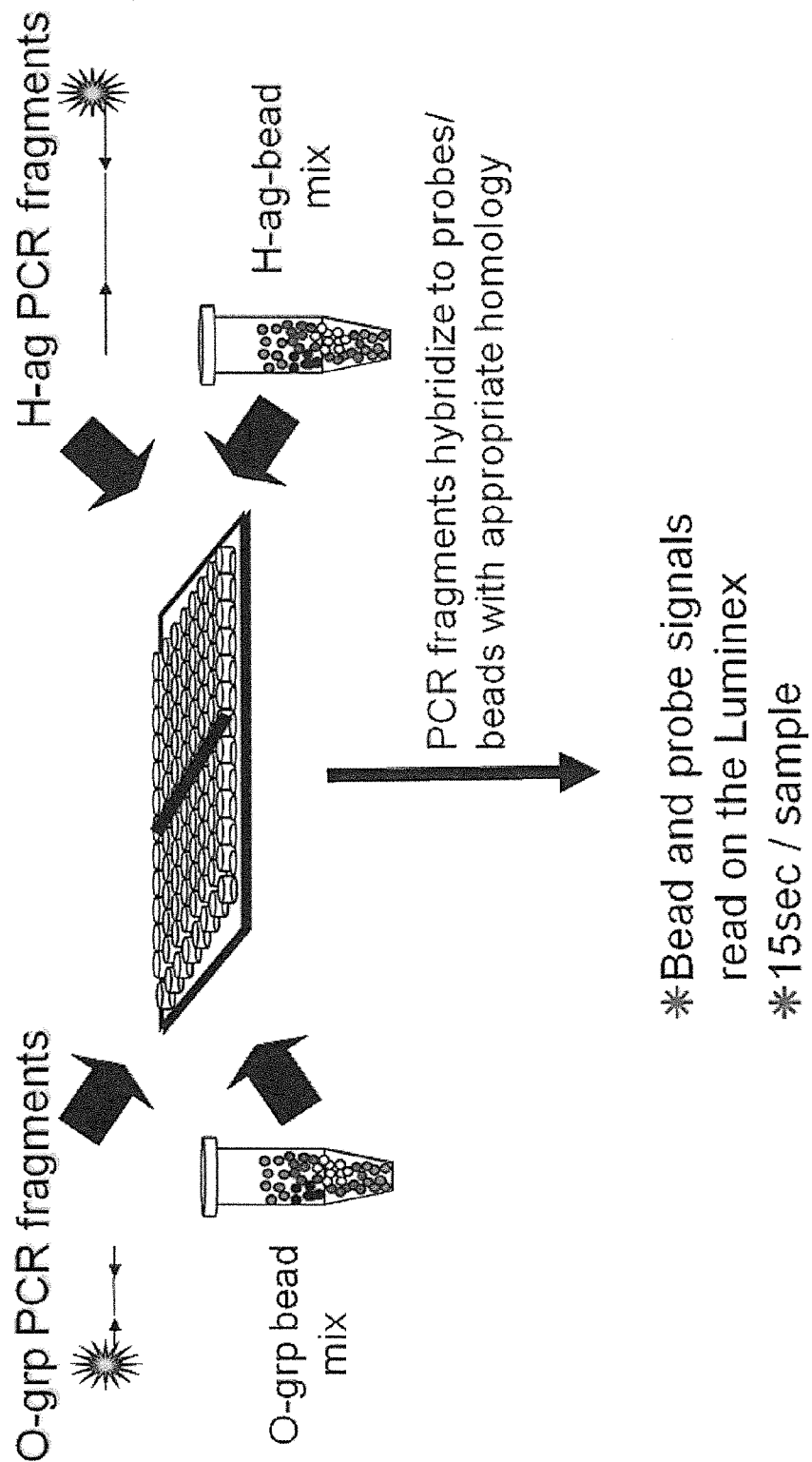
FIG. 4 is a schematic of a detection phase according to one embodiment.

The detection phase involves combining each set of PCR target amplicons with probe-coupled particles. A schematic of the detection phase is illustrated in FIG. 4. Immediately before use, 10 μl of microsphere solution per probe (Example 3), corresponding to approximately 2,500 coupled microspheres, were added to a final volume of 1 ml of 1.5×TMAC buffer (1.5 M tetramethylammonium chloride, 75 mM Tris, 6 mM EDTA, and 0.15% Sarkosyl [pH 8.0]). 33 μl of this particle mix was added to 5 μl of each group of PCR product (amplification phase) and 12 μl of TE buffer (Tris-EDTA pH 8.0) (Sigma-Aldrich, St. Louis, Mo.) in a low profile 96-well plate (BioRad, Hercules Calif.). This was mixed and incubated first at 94° C. for 5 minutes for DNA denaturation, followed by 30 minutes at 52° C. to allow hybridization of the probes to the target amplicons. Following the hybridization reaction, the 96-well plate containing the samples was moved to the brass heating plate in the BioPlex instrument preheated to 52° C. 75 μl of detection buffer (R-phycoerythrin-conjugated streptavidin (SAPE) (Invitrogen, Bethesda, Md.) diluted to 4 g/ml in 1×TMAC was mixed directly into the hybridization reaction. Samples were incubated for 10 minutes at 52° C. in the analyzer and then read by the BioPlex instrument (BioRad, Hercules, Calif.). The median fluorescence intensity (MFI) for each bead set was calculated automatically by the Bio-Plex software. A positive signal was defined as an MFI giving greater than 6 times the background fluorescence intensity for each bead-probe set. Machine-to-machine and run-to-run variation was normalized by calculating the ratio of the sample MFI to the negative control (P/N). Acceptable signal strength for each probe was approximately 1,000 with a relative background on high calibration setting of approximately 100 (P/N of 10). An arbitrary cutoff ratio of 6 times the background was established to score a particular isolate as positive or negative with each O-group-specific capture probe microsphere set.

For O-grp-1, an exemplary raw and ratio data averaged for five isolates for each O-group microsphere bead set are shown in FIG. 5. FIG. 5A illustrates raw MFI data illustrating specific detection of O-grp-1 serotype included in the isolate. FIG. 5B illustrates the ratio of positives to negative control for these isolates. For H-ag, FIG. 6A illustrates raw MFI data illustrating specific detection of H-antigens indicative of serotype included in the isolate, and FIG. 6B illustrates the ratio of positives to negative control for these isolates. These data illustrate the specific detection and serotyping capabilities of the assay.

Figure 7:
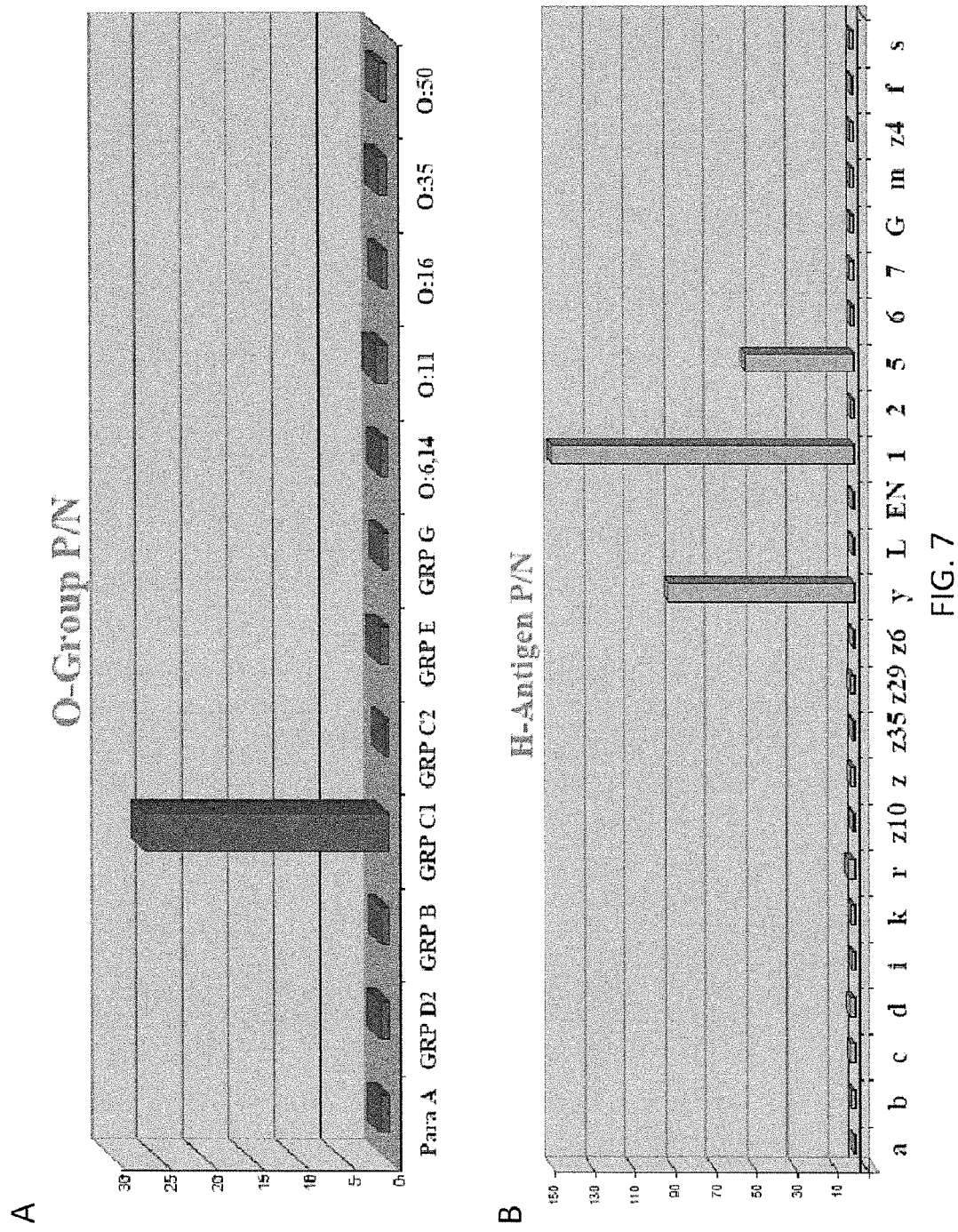
FIG. 7 illustrates one exemplary serotype revealing an O-grp C1 in a sample (A); and the H-ag results of the same isolate (B) illustrating formula 6,7:y:1,5 and identification of serotype Bareilly.

To determine the usefulness of the assay using unknown clinical isolates, 500 clinical isolates were evaluated in parallel with traditional serotyping methods. For the isolates, an O group could be determined by traditional methods, and the traditional and molecular methods identify the same O group for 94%; 6% of isolates possess an O group not detected in the assay. One exemplary serotype is illustrated in FIG. 7A which reveals an O-grp C1. A small number of isolates are designated "rough" by traditional serotyping, indicating that they did not express O antigen. Most isolates gave positive results for one of the serogroups covered in the assay. However, after combining the results with the H-ag targets each of these are successfully serotyped.

For the H-ag, the molecular serotyping results matched traditional H-antigen serotype completely for 415 (83%) of the isolates. Forty seven isolates (9.4%) possessed an antigen that was not detected in the assay. In all instances, the partial serotype determined for that isolate matched that of traditional serotyping. Twenty-seven isolates (5.4%) had no reaction with the probes as expected based on traditional serotyping, resulting in a partial serotype by H-ag molecular methods. At least some of these (e.g., lack of reactivity with H:5 or H:t probe) were known to be caused by allelic diversity.

When the results from the O-grp-1 and H-ag are combined, approximately 98% of the isolates are successfully serotyped. FIG. 7B illustrates the H-ag results of the same isolate as FIG. 7A. Combining these results yields a serotype formula of 6,7:y:1,5 which reveals that this isolate is K—W serotype Bareilly.

Figure 9:
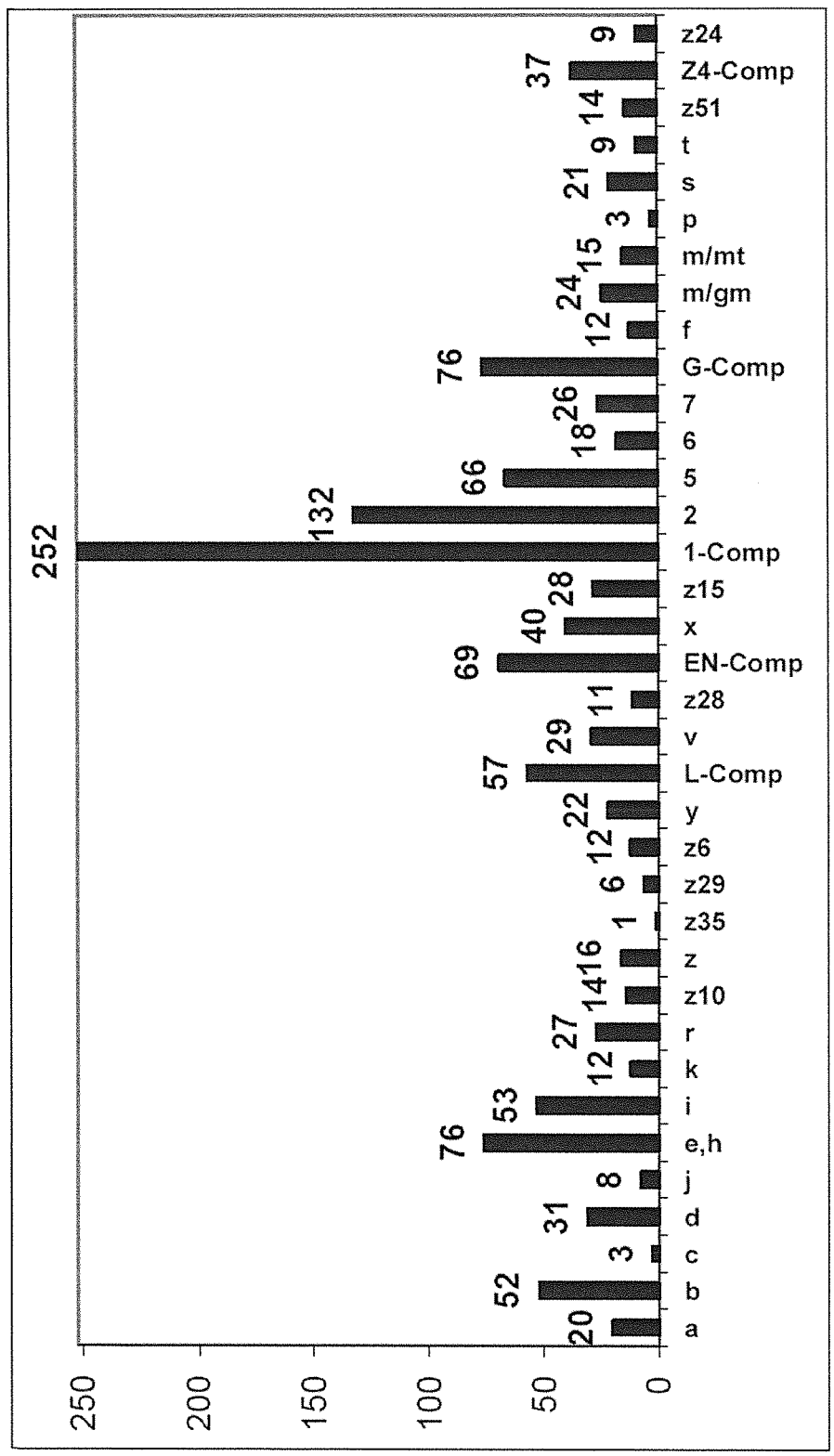
FIG. 9 illustrates the frequency of each of the H-ag antigens in the clinical isolates of FIG. 8.

Overall detection results of the 100 most common serotypes are illustrated in FIG. 8. The frequency of each of the H-ag antigens in the clinical isolates are illustrated in FIG. 9.

A small number of isolates are negative for O-grp-1 and H-ag targets analyzed. To determine whether a *Salmonella* serotype is present in these isolates, the above amplification and detection procedures are repeated with particle-bound probes and primers of O-grp-2 (Table 4) and additional targets (Table 3). Use of the O-grp-2 and additional targets probes and primers successfully identify several previously negative isolates.

Example 5

SE Assay

The probes specific for serotyping of *Salmonella* ser. Enteritidis in a sample as listed in Table 5 are coupled to particles as described in Example 3. Primers of Table 5 are used in an amplification reaction as described in Example 4 with a biotinylated reverse primer set. Genomic DNA from 25 poultry industry samples (broth cultures or washes) is prepared and used as template in an amplification phase. The resulting amplification products are then hybridized to the probe-coupled particles and analyzed as in Example 4. Eleven of the samples reveal a positive result for *Salmonella* ser. Enteritidis. The negative samples are then tested by the procedures of Example 4. Several of the remaining 14 isolates are successfully serotyped as other than Enteritidis by these procedures.

Example 6

Species and Subspecies Determination

The procedures of Example 4 are repeated using an assay for *Salmonella* species and subspecies identification. The probes of Table 6 are coupled with particles as per Example 3. An amplification reaction using the 500 clinical isolates is performed using the primers of Table 6 with the reverse primer biotinylated. Following the detection phase, the subspecies of each of the clinical isolates is successfully determined.

Example 7

Diagnosis of Infection in Human Subjects

A rapid method for early detection of *Salmonella* ser. Enteritidis infection is performed as a stand alone assay. The probes specific for serotyping of *Salmonella* ser. Enteritidis in a sample as listed in Table 5 are coupled to particles as described in Example 3. Primers of Table 5 are used in an amplification reaction as described in Example 4 with a biotinylated reverse primer set. Whole blood from 25 human subjects with a believed infection or a control are used as a source for preparation of DNA to serve as a template in an amplification phase. The resulting amplification products are then hybridized to probe-coupled particles using the probes of Table 5 and analyzed as in Example 4. One of the samples reveals a positive result for *Salmonella* ser. Enteritidis infection diagnosing infection in the subject.

Example 8

Diagnosis of Infection in Human Subjects

A rapid method for early detection of *Salmonella* infection is performed as a standalone assay. The probes as listed in Table 6 are coupled to particles as described in Example 3. Primers of Table 6 are used in an amplification reaction as described in Example 4 with a biotinylated reverse primer set. Stool samples from 25 human subjects with a believed infection or a control are used as a source for preparation of DNA to serve as a template in an amplification phase. The resulting amplification products are then hybridized to probe-coupled particles using the probes of Table 6 and analyzed as in Example 4. One of the samples reveals a positive result for *Salmonella enterica* subspecies I infection diagnosing infection in the subject.

REFERENCES

1. Baker, S., J. Hardy, K. E. Sanderson, M. Quail, I. Goodhead, R. A. Kingsley, J. Parkhill, B. Stocker, and G. Dougan. 2007. A novel linear plasmid mediates flagellar variation in *Salmonella Typhi*. PLoS Pathog 3:e59.
2. Boyd, E. F., F. S. Wang, T. S. Whittam, and R. K. Selander. 1996. Molecular genetic relationships of the *Salmonellae*. Appl Environ Microbiol 62:804-8.
3. Echeita, M. A., S. Herrera, J. Garaizar, and M. A. Usera. 2002. Multiplex PCR-based detection and identification of the most common *Salmonella* second-phase flagellar antigens. Res Microbiol 153:107-13.
4. Ewing, W. H. 1972. The nomenclature of *Salmonella*, its usage, and definitions for the three species. Can J Microbiol 18:1629-37.
5. Fitzgerald, C., M. Collins, S. van Duyne, M. Mikoleit, T. Brown, and P. Fields. 2007. Multiplex, bead-based suspension array for molecular determination of common *Salmonella* serogroups. J Clin Microbiol 45:3323-34.
6. Frankel, G. 1989. Intragenic recombination in a flagellin gene: characterization of the H1-j gene of *Salmonella typhi*. EMBO Journal 8:3149-52.
7. Garaizar, J., S. Porwollik, A. Echeita, A. Rementeria, S. Herrera, R. M. Wong, J. Frye, M. A. Usera, and M. McClelland. 2002. DNA microarray-based typing of an atypical monophasic *Salmonella enterica* serovar. J Clin Microbiol 40:2074-8.
8. Grimont, P. A. D., and F.-X. Weill. 2007. ANTIGENIC FORMULAE OF THE *SALMONELLA* SEROVARS. WHO Collaborating Centre for Reference and Research on *Salmonella*.
9. Guibourdenche, M., P. Roggentin, M. Mikoleit, P. I. Fields, J. Bockemuhl, P. A. Grimont, and F. X. Weill. 2009. Supplement 2003-2007 (No. 47) to the White-Kauffmann-Le Minor scheme. Res Microbiol.
10. Guibourdenche, M., P. Roggentin, M. Mikoleit, P. I. Fields, J. Bockemuhl, P. A. Grimont, and F. X. Weill. 2010. Supplement 2003-2007 (No. 47) to the White-Kauffinann-Le Minor scheme. Res Microbiol 161:26-9.
11. He, X. S., M. Rivkina, B. A. Stocker, and W. S. Robinson. 1994. Hypervariable region IV of *Salmonella* gene fliCd encodes a dominant surface epitope and a stabilizing factor for functional flagella. J Bacteriol 176:2406-14.
12. Herrera-Leon, S., J. R. McQuiston, M. A. Usera, P. I. Fields, J. Garaizar, and M. A. Echeita. 2004. Multiplex PCR for distinguishing the most common phase-1 flagellar antigens of *Salmonella* spp. J Clin Microbiol 42:2581-6.
13. Hirose, K., K. Itoh, H. Nakajima, T. Kurazono, M. Yamaguchi, K. Moriya, T. Ezaki, Y. Kawamura, K. Tamura, and H. Watanabe. 2002. Selective amplification of tyv (dbE), prt (dbS), viaB, and fliC genes by multiplex PCR for identification of *Salmonella enterica* serovars *Typhi* and Paratyphi A. J Clin Microbiol 40:633-6.
14. Joys, T. M. 1985. The covalent structure of the phase-1 flagellar filament protein of *Salmonella* typhimurium and its comparison with other flagellins. Journal of Biological Chemistry 260:15758-61.
15. Joys, T. M. 1969. Recombination in H1, the gene determining the flagellar antigen-i of *Salmonella* typhimurium; mapping of H1 and fla mutations. Journal of General Microbiology 58:267-75.
16. Kauffmann, F. 1966. The Bacteriology of Enterobacteriaceae, 1 ed, vol. The Williams and Wilkins Company, Baltimore.
17. Leader, B. T., J. G. Frye, J. Hu, P. J. Fedorka-Cray, and D. S. Boyle. 2009. High-throughput molecular determination of *Salmonella enterica* serovars by use of multiplex PCR and capillary electrophoresis analysis. J Clin Microbiol 47:1290-9.
18. MacNab, R. M. 1996. Flagella and Motility, p. 123-145. In F. C. Neidhardt (ed.), *Escherichia coli* and *Salmonella* Cellular and Molecular Biology, 2 ed, vol. 1. ASM Press, Washington, D.C.
19. Macnab, R. M. 1992. Genetics and biogenesis of bacterial flagella. Annu Rev Genet 26:131-58.
20. Masten, B. J., and T. M. Joys. 1993. Molecular analyses of the *Salmonella* g . . . flagellar antigen complex [published erratum appears in J Bacteriol 1994 16 May; 176(9):2771]. Journal of Bacteriology 175:5359-65.
21. McQuiston, J. R., P. I. Fields, R. V. Tauxe, and J. M. Logsdon, Jr. 2008. Do *Salmonella* carry spare tyres? Trends Microbiol 16:142-8.
22. McQuiston, J. R., S. Herrera-Leon, B. C. Wertheim, J. Doyle, P. I. Fields, R. V. Tauxe, and J. M. Logsdon, Jr. 2008. Molecular phylogeny of the *Salmonellae*: relationships among *Salmonella* species and subspecies determined from four housekeeping genes and evidence of lateral gene transfer events. J Bacteriol 190:7060-7.
23. McQuiston, J. R., R. Parrenas, M. Ortiz-Rivera, L. Gheesling, F. Brenner, and P. I. Fields. 2004. Sequencing and comparative analysis of flagellin genes fliC, fljB, and flpA from *Salmonella*. J Clin Microbiol 42:1923-32.
24. Microbiology, S. S. o. t. I. S. o. 1934. The Genus *Salmonella* Lignieres, 1900. Journal of Hygiene 22:333-350.
25. Popoff, M. Y., J. Bockemuhl, and L. L. Gheesling. 2004. Supplement 2002 (no. 46) to the Kauffmann-White scheme. Res Microbiol 155:568-70.
26. Prevention, C. f. D. C. a. 2004, posting date. Salmonella: Annual Summary. Dept. of Health and Human Services. [Online.]
27. Prokaryotes, J. C. o. t. I. C. o. S. o. 2005. The type species of the genus *Salmonella* Lignieres 1900 is *Salmonella*

*enterica* (ex Kauffmann and Edwards 1952) Le Minor and Popoff 1987, with the type strain LT2T, and conservation of the epithet *enterica* in *Salmonella enterica* over all earlier epithets that may be applied to this species. Opinion 80. Int J Syst Evol Microbiol 55:519-20.
28. Reeves, M. W., G. M. Evins, A. A. Heiba, B. D. Plikaytis, and J. J. Farmer, 3rd. 1989. Clonal nature of *Salmonella typhi* and its genetic relatedness to other *Salmonellae* as shown by multilocus enzyme electrophoresis, and proposal of *Salmonella bongori* comb. nov. J Clin Microbiol 27:313-20.
29. Services, D. o. H. a. H. 2001. *Salmonella*: Annual Summary 2001. Centers for Disease Control and Prevention.
30. Silverman, M., and M. Simon. 1980. Phase variation: genetic analysis of 45 switching mutants. Cell 19:845-54.
31. Silverman, M., J. Zieg, M. Hilmen, and M. Simon. 1979. Phase variation in *Salmonella*: genetic analysis of a recombinational switch. Proc Natl Acad Sci USA 76:391-5.
32. Smith, N. H., and R. K. Selander. 1991. Molecular genetic basis for complex flagellar antigen expression in a triphasic serovar of *Salmonella*. Proc Natl Acad Sci USA 88:956-60.
33. Tindall, B. J., P. A. Grimont, G. M. Garrity, and J. P. Euzeby. 2005. Nomenclature and taxonomy of the genus *Salmonella*. Int J Syst Evol Microbiol 55:521-4.
34. Trafny, E. A., K. Kozlowska, and M. Szpakowska. 2006. A novel multiplex PCR assay for the detection of *Salmonella enterica* serovar Enteritidis in human feces. Lett Appl Microbiol 43:673-9.
35. Vanegas, R. A., and T. M. Joys. 1995. Molecular analyses of the phase-2 antigen complex 1, 2, . . . of *Salmonella* spp. J Bacteriol 177:3863-4.
36. Wei, L. N., and T. M. Joys. 1985. Covalent structure of three phase-1 flagellar filament proteins of *Salmonella*. J Mol Biol 186:791-803.
37. Wei, L. N., and T. M. Joys. 1986. The nucleotide sequence of the H-1r gene of *Salmonella* rubislaw. Nucleic Acids Res 14:8227.
36. McQuiston, J. R., Waters, R. J., Dinsmore, B. A., Mikoleit, M. L. and Fields, P. I. 2011. Molecular determination of H antigens of *Salmonella* by use of a microsphere-based liquid array. J Clin Microbiol 49:565-573.

Methods involving conventional biological techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; Current Protocols in Molecular Biology, ed. Ausubel et al., Greene Publishing and Wiley-Interscience, New York, 1992 (with periodic updates); and Short Protocols in Molecular Biology, ed. Ausubel et al., 52 ed., Wiley-Interscience, New York, 2002. Immunological methods (e.g., preparation of antigen specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Additional protocols such as PCR Protocols can be found in "A Guide to Methods and Applications" Academic Press, NY.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

---

The invention claimed is:

1. A process of detecting the presence or absence of *Salmonella* in a sample comprising:
   adding to a sample one or more O-group-2 (O-grp-2) primer sets operable to produce an O-grp-2 amplification product of an O-grp-2 target sequence;
   said primer set comprising a forward primer and a reverse primer that hybridize to distinct regions flanking said O-grp-2 target sequence under conditions suitable for a polymerase chain reaction; and
   detecting the presence or absence of said O-grp-2 amplification product by hybridization of one or more labeled probes specific to said O-grp-2 amplification product, said labeled probe comprising a label and a nucleotide sequence, said nucleotide sequence comprising the sequence of SEQ ID NO: 134.

2. The process of claim 1 further comprising detecting the presence or absence of one or more O-group-1 (O-grp-1) amplification products, one or more H-antigen (H-ag) amplification products, or both.

3. The process of claim 1 wherein said detecting the presence or absence of said O-grp-2 amplification product is performed in the same sample with detection of one or more O-grp-1 amplification products, one or more H-ag amplification products, or both.

4. The process of claim 1 wherein at least one of said forward primers comprises the nucleotide sequence of any one or more of SEQ ID NOs: 83, 84, 85, 92, 93, 94, 95, 96, 107, 109, 111, 113, or 115.

5. The process of claim 1 wherein at least one of said reverse primers comprises the nucleotide sequence of any one or more of SEQ ID NOs: 86, 87, 88, 97, 98, 99, 100, 101, 108, 110, 112, 114, or 116.

6. The process of claim 1 wherein said nucleotide sequence consists of the sequence of SEQ ID NO: 134.

7. The process of claim 1 wherein said detecting diagnoses Salmonella infection in a subject.

* * * * *

SEQUENCE LISTING

<160> NUMBER OF SEQ ID NOS: 135

<210> SEQ ID NO 1
<211> LENGTH: 21
<212> TYPE: DNA
<213> ORGANISM: Salmonella

<400> SEQUENCE: 1
gagtttatat gcatatacta a                                              21

<210> SEQ ID NO 2
<211> LENGTH: 24
<212> TYPE: DNA
<213> ORGANISM: Salmonella

<400> SEQUENCE: 2
gcataaaaca tcatctctca taaa                                           24

<210> SEQ ID NO 3
<211> LENGTH: 19
<212> TYPE: DNA
<213> ORGANISM: Salmonella

<400> SEQUENCE: 3

-continued

```
gctttaatcc aatataaaa                                                19

<210> SEQ ID NO 4
<211> LENGTH: 18
<212> TYPE: DNA
<213> ORGANISM: Salmonella

<400> SEQUENCE: 4
cagacgtttg ttttataa                                                 18

<210> SEQ ID NO 5
<211> LENGTH: 24
<212> TYPE: DNA
<213> ORGANISM: Salmonella

<400> SEQUENCE: 5
ctgatttaac cgggtattat ttat                                          24

<210> SEQ ID NO 6
<211> LENGTH: 19
<212> TYPE: DNA
<213> ORGANISM: Salmonella

<400> SEQUENCE: 6
ctcttgatga atgttatta                                                19

<210> SEQ ID NO 7
<211> LENGTH: 16
<212> TYPE: DNA
<213> ORGANISM: Salmonella

<400> SEQUENCE: 7
tactggtaaa cttatc                                                   16

<210> SEQ ID NO 8
<211> LENGTH: 16
<212> TYPE: DNA
<213> ORGANISM: Salmonella

<400> SEQUENCE: 8
tgctggtaaa tttatc                                                   16

<210> SEQ ID NO 9
<211> LENGTH: 26
<212> TYPE: DNA
<213> ORGANISM: Salmonella

<400> SEQUENCE: 9
cgcatatgtt gataattaaa atcttt                                        26

<210> SEQ ID NO 10
<211> LENGTH: 24
<212> TYPE: DNA
<213> ORGANISM: Salmonella

<400> SEQUENCE: 10
taaatatatg atagttccaa ataa                                          24

<210> SEQ ID NO 11
<211> LENGTH: 18
<212> TYPE: DNA
<213> ORGANISM: Salmonella
```

<400> SEQUENCE: 11
gatcgtacaa tcaatatc                                                    18

<210> SEQ ID NO 12
<211> LENGTH: 21
<212> TYPE: DNA
<213> ORGANISM: Salmonella

<400> SEQUENCE: 12
cttttctatg cagtggttta a                                                21

<210> SEQ ID NO 13
<211> LENGTH: 17
<212> TYPE: DNA
<213> ORGANISM: Salmonella

<400> SEQUENCE: 13
gttaacccct cctaata                                                     17

<210> SEQ ID NO 14
<211> LENGTH: 18
<212> TYPE: DNA
<213> ORGANISM: Salmonella

<400> SEQUENCE: 14
gcggcggcga actcattt                                                    18

<210> SEQ ID NO 15
<211> LENGTH: 18
<212> TYPE: DNA
<213> ORGANISM: Salmonella

<400> SEQUENCE: 15
gcggcggcga gttcattt                                                    18

<210> SEQ ID NO 16
<211> LENGTH: 18
<212> TYPE: DNA
<213> ORGANISM: Salmonella

<400> SEQUENCE: 16
gtggctgcga gttcattt                                                    18

<210> SEQ ID NO 17
<211> LENGTH: 33
<212> TYPE: DNA
<213> ORGANISM: Salmonella

<400> SEQUENCE: 17
tttattgcca aatcaagaac tttaatggtt tta                                   33

<210> SEQ ID NO 18
<211> LENGTH: 34
<212> TYPE: DNA
<213> ORGANISM: Salmonella

<400> SEQUENCE: 18
atgaaatgtc gacgcacata gaataagaat aagc                                  34

<210> SEQ ID NO 19
<211> LENGTH: 35
<212> TYPE: DNA
<213> ORGANISM: Salmonella

```
<400> SEQUENCE: 19
tccctctcac cgtaaacatg ttctaaacgt aaatt                        35

<210> SEQ ID NO 20
<211> LENGTH: 34
<212> TYPE: DNA
<213> ORGANISM: Salmonella

<400> SEQUENCE: 20
aggatatatg ttaaggctgt acttatacct agct                         34

<210> SEQ ID NO 21
<211> LENGTH: 33
<212> TYPE: DNA
<213> ORGANISM: Salmonella

<400> SEQUENCE: 21
atatatagat gtttattata tttgcattcc cca                          33

<210> SEQ ID NO 22
<211> LENGTH: 28
<212> TYPE: DNA
<213> ORGANISM: Salmonella

<400> SEQUENCE: 22
cgctgaacgt gcagaaagag tatgatgt                                28

<210> SEQ ID NO 23
<211> LENGTH: 23
<212> TYPE: DNA
<213> ORGANISM: Salmonella

<400> SEQUENCE: 23
aacgtgcaga aaaatatga tgt                                      23

<210> SEQ ID NO 24
<211> LENGTH: 24
<212> TYPE: DNA
<213> ORGANISM: Salmonella

<400> SEQUENCE: 24
gtgcaacaaa aatataaggt cagc                                    24

<210> SEQ ID NO 25
<211> LENGTH: 20
<212> TYPE: DNA
<213> ORGANISM: Salmonella

<400> SEQUENCE: 25
gcgaacgacg gtgaaactat                                         20

<210> SEQ ID NO 26
<211> LENGTH: 23
<212> TYPE: DNA
<213> ORGANISM: Salmonella

<400> SEQUENCE: 26
tccagcttca agaatgttac ggg                                     23

<210> SEQ ID NO 27
<211> LENGTH: 24
<212> TYPE: DNA
```

<213> ORGANISM: Salmonella

<400> SEQUENCE: 27
atctaatttc aaaaacgtta ctgg                                  24

<210> SEQ ID NO 28
<211> LENGTH: 21
<212> TYPE: DNA
<213> ORGANISM: Salmonella

<400> SEQUENCE: 28
aaaaagcctt ggaatggatg g                                     21

<210> SEQ ID NO 29
<211> LENGTH: 25
<212> TYPE: DNA
<213> ORGANISM: Salmonella

<400> SEQUENCE: 29
agctgggctt agataaatta gatgt                                 25

<210> SEQ ID NO 30
<211> LENGTH: 25
<212> TYPE: DNA
<213> ORGANISM: Salmonella

<400> SEQUENCE: 30
gcagaaaaaa tatgatgtga agagc                                 25

<210> SEQ ID NO 31
<211> LENGTH: 22
<212> TYPE: DNA
<213> ORGANISM: Salmonella

<400> SEQUENCE: 31
aactgccttc aattgtctta cc                                    22

<210> SEQ ID NO 32
<211> LENGTH: 18
<212> TYPE: DNA
<213> ORGANISM: Salmonella

<400> SEQUENCE: 32
cacccgctgc tgtcaatg                                         18

<210> SEQ ID NO 33
<211> LENGTH: 20
<212> TYPE: DNA
<213> ORGANISM: Salmonella

<400> SEQUENCE: 33
cggtcacctc aacgaagtag                                       20

<210> SEQ ID NO 34
<211> LENGTH: 27
<212> TYPE: DNA
<213> ORGANISM: Salmonella

<400> SEQUENCE: 34
tataaacatt tttgcttgat tgtaagg                               27

<210> SEQ ID NO 35
<211> LENGTH: 23

<212> TYPE: DNA
<213> ORGANISM: Salmonella

<400> SEQUENCE: 35
tagcagtata ttcagctccc att                                              23

<210> SEQ ID NO 36
<211> LENGTH: 23
<212> TYPE: DNA
<213> ORGANISM: Salmonella

<400> SEQUENCE: 36
atttattcgt cagcagtttt ttc                                              23

<210> SEQ ID NO 37
<211> LENGTH: 22
<212> TYPE: DNA
<213> ORGANISM: Salmonella

<400> SEQUENCE: 37
aaccgccttc aattgtttta cc                                               22

<210> SEQ ID NO 38
<211> LENGTH: 25
<212> TYPE: DNA
<213> ORGANISM: Salmonella

<400> SEQUENCE: 38
cgtcaataga ttttccattt ttatc                                            25

<210> SEQ ID NO 39
<211> LENGTH: 20
<212> TYPE: DNA
<213> ORGANISM: Salmonella

<400> SEQUENCE: 39
ccgcgttaac aaatgacagc                                                  20

<210> SEQ ID NO 40
<211> LENGTH: 19
<212> TYPE: DNA
<213> ORGANISM: Salmonella

<400> SEQUENCE: 40
ggcagattca aaacggttc                                                   19

<210> SEQ ID NO 41
<211> LENGTH: 21
<212> TYPE: DNA
<213> ORGANISM: Salmonella

<400> SEQUENCE: 41
gcatagccac catcaataac c                                                21

<210> SEQ ID NO 42
<211> LENGTH: 21
<212> TYPE: DNA
<213> ORGANISM: Salmonella

<400> SEQUENCE: 42
ccttcggcta cattaagcac t                                                21

<210> SEQ ID NO 43

-continued

```
<211> LENGTH: 20
<212> TYPE: DNA
<213> ORGANISM: Salmonella

<400> SEQUENCE: 43
tctacaactg atactggttc                                              20

<210> SEQ ID NO 44
<211> LENGTH: 22
<212> TYPE: DNA
<213> ORGANISM: Salmonella

<400> SEQUENCE: 44
tgcctatacg ccaaaaggta cc                                           22

<210> SEQ ID NO 45
<211> LENGTH: 21
<212> TYPE: DNA
<213> ORGANISM: Salmonella

<400> SEQUENCE: 45
ctggcgcagc tagcttgaaa g                                            21

<210> SEQ ID NO 46
<211> LENGTH: 26
<212> TYPE: DNA
<213> ORGANISM: Salmonella

<400> SEQUENCE: 46
actacaaaga aagttaatat tgatac                                       26

<210> SEQ ID NO 47
<211> LENGTH: 18
<212> TYPE: DNA
<213> ORGANISM: Salmonella

<400> SEQUENCE: 47
actggcgccg ataaggac                                                18

<210> SEQ ID NO 48
<211> LENGTH: 21
<212> TYPE: DNA
<213> ORGANISM: Salmonella

<400> SEQUENCE: 48
ggcgattcct tgtctgctac g                                            21

<210> SEQ ID NO 49
<211> LENGTH: 22
<212> TYPE: DNA
<213> ORGANISM: Salmonella

<400> SEQUENCE: 49
ttgataagac gaacggtgag gt                                           22

<210> SEQ ID NO 50
<211> LENGTH: 28
<212> TYPE: DNA
<213> ORGANISM: Salmonella

<400> SEQUENCE: 50
atggtttcct taaagttgac gttaatac                                     28
```

```
<210> SEQ ID NO 51
<211> LENGTH: 20
<212> TYPE: DNA
<213> ORGANISM: Salmonella

<400> SEQUENCE: 51
ggcacaccaa caggaccaat                                              20

<210> SEQ ID NO 52
<211> LENGTH: 20
<212> TYPE: DNA
<213> ORGANISM: Salmonella

<400> SEQUENCE: 52
aaccaacgaa tgcagttgaa                                              20

<210> SEQ ID NO 53
<211> LENGTH: 21
<212> TYPE: DNA
<213> ORGANISM: Salmonella

<400> SEQUENCE: 53
caattggggc ctcgactact a                                            21

<210> SEQ ID NO 54
<211> LENGTH: 21
<212> TYPE: DNA
<213> ORGANISM: Salmonella

<400> SEQUENCE: 54
tgctaagagc ggttactata a                                            21

<210> SEQ ID NO 55
<211> LENGTH: 18
<212> TYPE: DNA
<213> ORGANISM: Salmonella

<400> SEQUENCE: 55
tggcgcgcac aaagcaac                                                18

<210> SEQ ID NO 56
<211> LENGTH: 21
<212> TYPE: DNA
<213> ORGANISM: Salmonella

<400> SEQUENCE: 56
ttacagaccc agaaattgct g                                            21

<210> SEQ ID NO 57
<211> LENGTH: 21
<212> TYPE: DNA
<213> ORGANISM: Salmonella

<400> SEQUENCE: 57
aagcactacg atgcctactg c                                            21

<210> SEQ ID NO 58
<211> LENGTH: 21
<212> TYPE: DNA
<213> ORGANISM: Salmonella

<400> SEQUENCE: 58
aaaaggccaa ttagttacga t                                            21
```

```
<210> SEQ ID NO 59
<211> LENGTH: 21
<212> TYPE: DNA
<213> ORGANISM: Salmonella

<400> SEQUENCE: 59
aatgccgaca accactgaaa g                                              21

<210> SEQ ID NO 60
<211> LENGTH: 19
<212> TYPE: DNA
<213> ORGANISM: Salmonella

<400> SEQUENCE: 60
aaccgccgcg aaagtgaca                                                 19

<210> SEQ ID NO 61
<211> LENGTH: 18
<212> TYPE: DNA
<213> ORGANISM: Salmonella

<400> SEQUENCE: 61
cactgtaagt ggttatac                                                  18

<210> SEQ ID NO 62
<211> LENGTH: 24
<212> TYPE: DNA
<213> ORGANISM: Salmonella

<400> SEQUENCE: 62
cactgtaggt ggttataccg atgc                                           24

<210> SEQ ID NO 63
<211> LENGTH: 29
<212> TYPE: DNA
<213> ORGANISM: Salmonella

<400> SEQUENCE: 63
atattattcc actgtaagtg tgttatacc                                      29

<210> SEQ ID NO 64
<211> LENGTH: 23
<212> TYPE: DNA
<213> ORGANISM: Salmonella

<400> SEQUENCE: 64
ctgtaggtgt gttataccga tgc                                            23

<210> SEQ ID NO 65
<211> LENGTH: 26
<212> TYPE: DNA
<213> ORGANISM: Salmonella

<400> SEQUENCE: 65
caataatggt actcactgg atgtat                                          26

<210> SEQ ID NO 66
<211> LENGTH: 21
<212> TYPE: DNA
<213> ORGANISM: Salmonella

<400> SEQUENCE: 66
gtgtgtacga atggtactgg c                                              21
```

-continued

<210> SEQ ID NO 67
<211> LENGTH: 19
<212> TYPE: DNA
<213> ORGANISM: Salmonella

<400> SEQUENCE: 67
gtggtacgac tggtacggc                                                  19

<210> SEQ ID NO 68
<211> LENGTH: 24
<212> TYPE: DNA
<213> ORGANISM: Salmonella

<400> SEQUENCE: 68
gtacgcttgg cacggcttct gtaa                                            24

<210> SEQ ID NO 69
<211> LENGTH: 27
<212> TYPE: DNA
<213> ORGANISM: Salmonella

<400> SEQUENCE: 69
cgaatggtgc acctagtgta acaggta                                         27

<210> SEQ ID NO 70
<211> LENGTH: 25
<212> TYPE: DNA
<213> ORGANISM: Salmonella

<400> SEQUENCE: 70
acggtaatgg tacggtttct actac                                           25

<210> SEQ ID NO 71
<211> LENGTH: 24
<212> TYPE: DNA
<213> ORGANISM: Salmonella

<400> SEQUENCE: 71
cggtcgaatg ttgatgtctg ctac                                            24

<210> SEQ ID NO 72
<211> LENGTH: 18
<212> TYPE: DNA
<213> ORGANISM: Salmonella

<400> SEQUENCE: 72
tattgccact ggcgcgac                                                   18

<210> SEQ ID NO 73
<211> LENGTH: 25
<212> TYPE: DNA
<213> ORGANISM: Salmonella

<400> SEQUENCE: 73
gtttatactt ccgttgtaag cggtc                                           25

<210> SEQ ID NO 74
<211> LENGTH: 23
<212> TYPE: DNA
<213> ORGANISM: Salmonella

<400> SEQUENCE: 74
tgatattgcc attggcgctg gcg                                           23

<210> SEQ ID NO 75
<211> LENGTH: 28
<212> TYPE: DNA
<213> ORGANISM: Salmonella

<400> SEQUENCE: 75
ctgcggttaa cctattcata gacgacta                                      28

<210> SEQ ID NO 76
<211> LENGTH: 30
<212> TYPE: DNA
<213> ORGANISM: Salmonella

<400> SEQUENCE: 76
gctccaactg ttcctgataa agtatacgta                                    30

<210> SEQ ID NO 77
<211> LENGTH: 27
<212> TYPE: DNA
<213> ORGANISM: Salmonella

<400> SEQUENCE: 77
tattaattct ggagcagtaa ctgatga                                       27

<210> SEQ ID NO 78
<211> LENGTH: 22
<212> TYPE: DNA
<213> ORGANISM: Salmonella

<400> SEQUENCE: 78
accgagctgg gcttagataa at                                            22

<210> SEQ ID NO 79
<211> LENGTH: 24
<212> TYPE: DNA
<213> ORGANISM: Salmonella

<400> SEQUENCE: 79
gctaccgtag ataatagtac tggg                                          24

<210> SEQ ID NO 80
<211> LENGTH: 24
<212> TYPE: DNA
<213> ORGANISM: Salmonella

<400> SEQUENCE: 80
tacctcaata ccgctggtct taat                                          24

<210> SEQ ID NO 81
<211> LENGTH: 26
<212> TYPE: DNA
<213> ORGANISM: Salmonella

<400> SEQUENCE: 81
atgaaggtaa tgtgtacggt ttctac                                        26

<210> SEQ ID NO 82
<211> LENGTH: 23
<212> TYPE: DNA
<213> ORGANISM: Salmonella

<400> SEQUENCE: 82
cagctgattt cgataacgca aaa                                                23

<210> SEQ ID NO 83
<211> LENGTH: 18
<212> TYPE: DNA
<213> ORGANISM: Salmonella

<400> SEQUENCE: 83
gtggtggctg gcgaatgg                                                      18

<210> SEQ ID NO 84
<211> LENGTH: 25
<212> TYPE: DNA
<213> ORGANISM: Salmonella

<400> SEQUENCE: 84
aggttatttc agcataagga gactt                                              25

<210> SEQ ID NO 85
<211> LENGTH: 21
<212> TYPE: DNA
<213> ORGANISM: Salmonella

<400> SEQUENCE: 85
cctggatgac acaggtaagc c                                                  21

<210> SEQ ID NO 86
<211> LENGTH: 20
<212> TYPE: DNA
<213> ORGANISM: Salmonella

<400> SEQUENCE: 86
ggagaggcgg tttgatgtgg                                                    20

<210> SEQ ID NO 87
<211> LENGTH: 21
<212> TYPE: DNA
<213> ORGANISM: Salmonella

<400> SEQUENCE: 87
ctcttccata ccactttccg a                                                  21

<210> SEQ ID NO 88
<211> LENGTH: 18
<212> TYPE: DNA
<213> ORGANISM: Salmonella

<400> SEQUENCE: 88
tgggtcagca gcgacaga                                                      18

<210> SEQ ID NO 89
<211> LENGTH: 20
<212> TYPE: DNA
<213> ORGANISM: Salmonella

<400> SEQUENCE: 89
tactccctga atctgagaaa                                                    20

<210> SEQ ID NO 90
<211> LENGTH: 21
<212> TYPE: DNA
<213> ORGANISM: Salmonella

<400> SEQUENCE: 90
gacggagcag agagattatc g                                        21

<210> SEQ ID NO 91
<211> LENGTH: 30
<212> TYPE: DNA
<213> ORGANISM: Salmonella

<400> SEQUENCE: 91
ataacattgg ttatcaaaaa ccttccaaaa                               30

<210> SEQ ID NO 92
<211> LENGTH: 25
<212> TYPE: DNA
<213> ORGANISM: Salmonella

<400> SEQUENCE: 92
agaggaataa aaaattttac gttgt                                    25

<210> SEQ ID NO 93
<211> LENGTH: 21
<212> TYPE: DNA
<213> ORGANISM: Salmonella

<400> SEQUENCE: 93
gcatggatgg gtggaattag t                                        21

<210> SEQ ID NO 94
<211> LENGTH: 23
<212> TYPE: DNA
<213> ORGANISM: Salmonella

<400> SEQUENCE: 94
attgttgcat ttgtaaaatg tat                                      23

<210> SEQ ID NO 95
<211> LENGTH: 23
<212> TYPE: DNA
<213> ORGANISM: Salmonella

<400> SEQUENCE: 95
cgatggtcca ttatttgatt ctt                                      23

<210> SEQ ID NO 96
<211> LENGTH: 23
<212> TYPE: DNA
<213> ORGANISM: Salmonella

<400> SEQUENCE: 96
ataatcctga aaatggtata act                                      23

<210> SEQ ID NO 97
<211> LENGTH: 25
<212> TYPE: DNA
<213> ORGANISM: Salmonella

<400> SEQUENCE: 97
attgttttcc ttaaattaat cctca                                    25

<210> SEQ ID NO 98
<211> LENGTH: 19
<212> TYPE: DNA
<213> ORGANISM: Salmonella

-continued

```
<400> SEQUENCE: 98
gagccatgcc catatcagc                                              19

<210> SEQ ID NO 99
<211> LENGTH: 21
<212> TYPE: DNA
<213> ORGANISM: Salmonella

<400> SEQUENCE: 99
aacaccatgc atcttaacta a                                           21

<210> SEQ ID NO 100
<211> LENGTH: 22
<212> TYPE: DNA
<213> ORGANISM: Salmonella

<400> SEQUENCE: 100
ggggaagacc ttcagataaa ga                                          22

<210> SEQ ID NO 101
<211> LENGTH: 23
<212> TYPE: DNA
<213> ORGANISM: Salmonella

<400> SEQUENCE: 101
atgtttcgcc atataaaata tga                                         23

<210> SEQ ID NO 102
<211> LENGTH: 33
<212> TYPE: DNA
<213> ORGANISM: Salmonella

<400> SEQUENCE: 102
gaatctgtcc tctgtaatta ttaataatga ttg                              33

<210> SEQ ID NO 103
<211> LENGTH: 33
<212> TYPE: DNA
<213> ORGANISM: Salmonella

<400> SEQUENCE: 103
aaaaataact taaaaattt aatacattag aaa                               33

<210> SEQ ID NO 104
<211> LENGTH: 37
<212> TYPE: DNA
<213> ORGANISM: Salmonella

<400> SEQUENCE: 104
gcctattaga tagattaaat aaaatacaga tccaaag                          37

<210> SEQ ID NO 105
<211> LENGTH: 32
<212> TYPE: DNA
<213> ORGANISM: Salmonella

<400> SEQUENCE: 105
actggattag tgaaaatatt aattctataa tc                               32

<210> SEQ ID NO 106
<211> LENGTH: 35
<212> TYPE: DNA
```

<213> ORGANISM: Salmonella

<400> SEQUENCE: 106
cgcaggccct ctaaatatcc ctaatattat agtgg     35

<210> SEQ ID NO 107
<211> LENGTH: 26
<212> TYPE: DNA
<213> ORGANISM: Salmonella

<400> SEQUENCE: 107
ctgctttctc tacttaacag tgctcg     26

<210> SEQ ID NO 108
<211> LENGTH: 22
<212> TYPE: DNA
<213> ORGANISM: Salmonella

<400> SEQUENCE: 108
cgcatcaata ataccggcct tc     22

<210> SEQ ID NO 109
<211> LENGTH: 22
<212> TYPE: DNA
<213> ORGANISM: Salmonella

<400> SEQUENCE: 109
atgatgcgcg tactggttgt ag     22

<210> SEQ ID NO 110
<211> LENGTH: 27
<212> TYPE: DNA
<213> ORGANISM: Salmonella

<400> SEQUENCE: 110
tttgatgacc tcttcattga cggataa     27

<210> SEQ ID NO 111
<211> LENGTH: 21
<212> TYPE: DNA
<213> ORGANISM: Salmonella

<400> SEQUENCE: 111
gagtttatat gcatatacta a     21

<210> SEQ ID NO 112
<211> LENGTH: 16
<212> TYPE: DNA
<213> ORGANISM: Salmonella

<400> SEQUENCE: 112
tactggtaaa cttatc     16

<210> SEQ ID NO 113
<211> LENGTH: 23
<212> TYPE: DNA
<213> ORGANISM: Salmonella

<400> SEQUENCE: 113
tccagcttca agaatgttac ggg     23

<210> SEQ ID NO 114
<211> LENGTH: 27

<212> TYPE: DNA
<213> ORGANISM: Salmonella

<400> SEQUENCE: 114
tataaacatt tttgcttgat tgtaagg    27

<210> SEQ ID NO 115
<211> LENGTH: 18
<212> TYPE: DNA
<213> ORGANISM: Salmonella

<400> SEQUENCE: 115
gtggtggctg gcgaatgg    18

<210> SEQ ID NO 116
<211> LENGTH: 20
<212> TYPE: DNA
<213> ORGANISM: Salmonella

<400> SEQUENCE: 116
ggagaggcgg tttgatgtgg    20

<210> SEQ ID NO 117
<211> LENGTH: 25
<212> TYPE: DNA
<213> ORGANISM: Salmonella

<400> SEQUENCE: 117
cctggcggtg ggttttgttg tcttc    25

<210> SEQ ID NO 118
<211> LENGTH: 19
<212> TYPE: DNA
<213> ORGANISM: Salmonella

<400> SEQUENCE: 118
tccaggattc aggtcacca    19

<210> SEQ ID NO 119
<211> LENGTH: 18
<212> TYPE: DNA
<213> ORGANISM: Salmonella

<400> SEQUENCE: 119
ccttaatgaa caccttcc    18

<210> SEQ ID NO 120
<211> LENGTH: 18
<212> TYPE: DNA
<213> ORGANISM: Salmonella

<400> SEQUENCE: 120
gcggcggcga gttcattt    18

<210> SEQ ID NO 121
<211> LENGTH: 25
<212> TYPE: DNA
<213> ORGANISM: Salmonella

<400> SEQUENCE: 121
acggtaatgg tacggtttct actac    25

<210> SEQ ID NO 122

-continued

```
<211> LENGTH: 18
<212> TYPE: DNA
<213> ORGANISM: Salmonella

<400> SEQUENCE: 122
tattgccact ggcgcgac                                                   18

<210> SEQ ID NO 123
<211> LENGTH: 20
<212> TYPE: DNA
<213> ORGANISM: Salmonella

<400> SEQUENCE: 123
tactccctga atctgagaaa                                                 20

<210> SEQ ID NO 124
<211> LENGTH: 20
<212> TYPE: DNA
<213> ORGANISM: Salmonella

<400> SEQUENCE: 124
taccttaatg aacaccttcc                                                 20

<210> SEQ ID NO 125
<211> LENGTH: 17
<212> TYPE: DNA
<213> ORGANISM: Salmonella

<400> SEQUENCE: 125
ggcctgtcct taatacg                                                    17

<210> SEQ ID NO 126
<211> LENGTH: 22
<212> TYPE: DNA
<213> ORGANISM: Salmonella

<400> SEQUENCE: 126
tgacgtttta ctaccggttc tg                                              22

<210> SEQ ID NO 127
<211> LENGTH: 21
<212> TYPE: DNA
<213> ORGANISM: Salmonella

<400> SEQUENCE: 127
tgccagtgct ggtgttaacc g                                               21

<210> SEQ ID NO 128
<211> LENGTH: 20
<212> TYPE: DNA
<213> ORGANISM: Salmonella

<400> SEQUENCE: 128
tcgatgcagc agaagatgcc                                                 20

<210> SEQ ID NO 129
<211> LENGTH: 22
<212> TYPE: DNA
<213> ORGANISM: Salmonella

<400> SEQUENCE: 129
ggcaagataa agtctgtagg tt                                              22
```

```
<210> SEQ ID NO 130
<211> LENGTH: 24
<212> TYPE: DNA
<213> ORGANISM: Salmonella

<400> SEQUENCE: 130
gagcatcgcc ggacatcgcg attg                                          24

<210> SEQ ID NO 131
<211> LENGTH: 34
<212> TYPE: DNA
<213> ORGANISM: Salmonella

<400> SEQUENCE: 131
gaatctgtcc tctgtaactt attaataatg attg                               34

<210> SEQ ID NO 132
<211> LENGTH: 35
<212> TYPE: DNA
<213> ORGANISM: Salmonella

<400> SEQUENCE: 132
ccaagtatat gcagataata gggtaaaatc agaat                              35

<210> SEQ ID NO 133
<211> LENGTH: 39
<212> TYPE: DNA
<213> ORGANISM: Salmonella

<400> SEQUENCE: 133
gacatatgag atatacaaac ctattttata ataccctttg                         39

<210> SEQ ID NO 134
<211> LENGTH: 38
<212> TYPE: DNA
<213> ORGANISM: Salmonella

<400> SEQUENCE: 134
cctgtaaaaa tatacctatt gtctataaaa tagctctt                           38

<210> SEQ ID NO 135
<211> LENGTH: 35
<212> TYPE: DNA
<213> ORGANISM: Salmonella

<400> SEQUENCE: 135
attattgtaa attgccattt aaacactttt ttagc                              35
```